United States Patent
Abdelfatah et al.

(10) Patent No.: US 11,708,276 B2
(45) Date of Patent: Jul. 25, 2023

(54) DISPERSION OF BARE NANOPARTICLES IN NONPOLAR SOLVENTS

(71) Applicant: UTI LIMITED PARTNERSHIP, Calgary (CA)

(72) Inventors: Elsayed Abdelfatah, Calgary (CA); Steven Bryant, Calgary (CA)

(73) Assignee: UTI LIMITED PARTNERSHIP, Calgary (CA)

( * ) Notice: Subject to any disclaimer, the term of this patent is extended or adjusted under 35 U.S.C. 154(b) by 63 days.

(21) Appl. No.: 16/864,313

(22) Filed: May 1, 2020

(65) Prior Publication Data

US 2020/0346942 A1    Nov. 5, 2020

Related U.S. Application Data

(60) Provisional application No. 62/843,200, filed on May 3, 2019.

(51) Int. Cl.
| | | |
|---|---|---|
| C01B 33/18 | (2006.01) | |
| C01G 49/08 | (2006.01) | |
| C01B 33/12 | (2006.01) | |
| C09C 1/56 | (2006.01) | |
| C01B 32/914 | (2017.01) | |
| C01B 32/174 | (2017.01) | |
| B22F 1/0545 | (2022.01) | |
| B82Y 40/00 | (2011.01) | |

(52) U.S. Cl.
CPC ............ *C01B 33/18* (2013.01); *B22F 1/0545* (2022.01); *C01B 32/174* (2017.08); *C01B 32/914* (2017.08); *C01B 33/12* (2013.01); *C01G 49/08* (2013.01); *C09C 1/56* (2013.01); *B82Y 40/00* (2013.01); *C01P 2004/64* (2013.01)

(58) Field of Classification Search
CPC ..... C01G 49/08; C01B 32/174; C01B 32/914; C01B 33/12; C01B 33/18; C09C 15/56; B82Y 40/00
USPC .......................................................... 428/402
See application file for complete search history.

(56) References Cited

U.S. PATENT DOCUMENTS

| | | | |
|---|---|---|---|
| 8,920,682 B2 | 12/2014 | Texter | |
| 2007/0265379 A1* | 11/2007 | Chen | B82Y 30/00 524/495 |
| 2013/0221289 A1* | 8/2013 | Arce Arce | C09K 11/661 252/301.36 |

FOREIGN PATENT DOCUMENTS

| | | | |
|---|---|---|---|
| CN | 104927971 A | * | 9/2015 |
| WO | 2013/096540 A1 | | 6/2013 |

OTHER PUBLICATIONS

He "Nanoparticles in ionic liquids: interactions and organization" Phys.Chem.Chem.Phys., 2015, 17, 18238 (Year: 2015).*

(Continued)

*Primary Examiner* — Tri V Nguyen
(74) *Attorney, Agent, or Firm* — FisherBroyles LLP; Anthony Dovale

(57) ABSTRACT

Methods are disclosed for dispersing nanoparticles in solvents, involving the use of a cationic species and an anionic species, where at least one of the ionic species is soluble in the nonpolar solvent and the other ionic species has a relatively strong affinity for the surface of the nanoparticles. The cationic species and the anionic species together form a cluster of ion pairs shielding the nanoparticles and enhancing their dispersibility in the nonpolar solvent.

18 Claims, 7 Drawing Sheets

(56) References Cited

OTHER PUBLICATIONS

Thawarkar "Plasmonic behavior of ionic liquid stabilized gold nanoparticles in molecular solvents." NewJ.Chem., 2017, 41, 12989 (Year: 2017).*

Comiskey, B., Albert, J. D., Yoshizawa, H., Jacobson, J. 1998. An electrophoretic ink for all-printed reflective electronic displays. Nature 394: 253. 10.1038/28349.

Hao, T. 2001. Electrorheological Fluids. Advanced Materials 13 (24): 1847-1857. doi:10.1002/1521-4095(200112) 13:24<1847::AID-ADMA1847>3.0.CO;2-A.

Jones, S. A., Martin, G. P., Brown, M. B. 2006. Manipulation of Beclomethasone–Hydrofluoroalkane Interactions using Biocompatible Macromolecules. Journal of Pharmaceutical Sciences 95 (5): 1060-1074. 10.1002/ps.20608.

León, O., Rogel, E., Urbina, A., Andujar, A., Lucas, A. 1999. Study of the Adsorption of Alkyl Benzene-Derived Amphiphiles on Asphaltene Particles Langmuir 15 (22): 7653-7657. 10.1021/la9812370.

Li, Z., Zhu, Y. 2003. Surface-modification of $SiO_2$ nanoparticles with oleic acid. Applied Surface Science 211 (1): 315-320. http://doi.org/10.1016/S0169-4332(03)00259-9.

McCrary, P. D., Beasley, P. A., Gurau, G., Narita, A., Barber, P. S., Cojocaru, O. A., Rogers, R. D. 2013. Drug specific, tuning of an ionic liquid's hydrophilic-lipophilic balance to improve water solubility of poorly soluble active pharmaceutical ingredients. New Journal of Chemistry 37 (7): 2196-2202. http://doi.org/10.1039/C3NJ00454F.

Morrison, I. D. 1993. Electrical charges in nonaqueous media. Colloids and Surfaces A: Physicochemical and Engineering Aspects 71 (1): 1-37. https://doi.org/10.1016/0927-7757(93)80026-B.

Poovarodom, S., Berg, J. C. 2010. Effect of particle and surfactant acid-base properties on charging of colloids in apolar media Journal of Colloid and Interface Science 346 (2): 370-377. https://doi.org/10.1016/j.jcis 2010.03.012.

Ryoo, W., Webber, S. E., Bonnecaze, R. T., Johnston, K. P. 2006. Long-Ranged Electrostatic Repulsion and Crystallization of Emulsion Droplets in an Ultralow Dielectric Medium Supercritical Carbon Dioxide. Langmuir 22 (3) 1006-1015. 10.1021/la052298i.

Sainis, S. K., Germain, V., Mejean, C. O., Dufresne, E. R. 2008. Electrostatic Interactions of Colloidal Particles in Nonpolar Solvents: Role of Surface Chemistry and Charge Control Agents. Langmuir 24 (4): 1160-1164. 10.1021/a702432u.

* cited by examiner

DISPERSION OF BARE NANOPARTICLES IN NONPOLAR SOLVENTS

FIELD OF THE INVENTION

Innovations are disclosed in the field of organic chemistry, related to dispersions of solid nanoparticles decorated with ionic species in nonpolar solvents.

BACKGROUND

Nonpolar solvents (e.g. toluene, hexanes, dodecanes, $scCO_2$, etc.) have very low dielectric constants. This leads to the absence of electric double layer and poor solvency of bare metal oxide nanoparticles in such solvents which make the nanoparticles non-dispersible in these media. Several methods are available to stabilize the nanoparticles in these solvents. Surface modification of nanoparticles using organic molecules can assist the stability in nonpolar solvents (Li and Zhu 2003). However, this method is not trivial and involved complex steps of covalently bonding such as esterification and amidization, and purification which is not feasible for scale up processes.

Nanoparticles dispersions in nonaqueous nonpolar media has gained a wide interest recently due to promising applications. While polymer adsorption on nanoparticles can sterically stabilize the dispersion, several applications need charged particles in nonpolar media. The importance of these charged dispersions is sensed in many fields such as liquid immersion development (LID), electrostatic lithography, drop-on-demand ink jet, photoelectrophoresis, electrophoretic displays, and electrorheological fluids (Morrison 1993, Comiskey et al. 1998, Hao 2001, Sainis et al. 2008). Other applications that require electrostatic repulsions such as prevention of asphaltene precipitation in oil reservoirs (León et al. 1999), dispersion of nanoparticles in $scCO_2$ (Ryoo et al. 2006), and stabilization of particles for airborne drug delivery (Jones et al. 2006).

provided a comprehensive literature review of the electrical charges in nonaqueous media along with the key applications of such dispersions. In general particles charge is due to either specific adsorption of ions from the solution or dissociation of the groups on the surface of the particles. Existence of water even in very low content in the nonpolar solvents can significantly affect the charging of the particles as it affects the formation ions structures and the surface chemistry of the particles.

Poovarodom and Berg (2010) studied the effect of acid-base properties on charging of colloids in apolar media. In their study the nanoparticles were initially surface functionalized with either acid or base and then dispersed in apolar solvents that contains either acid or base surfactants. They found that at high enough surfactant concentration (above the critical micelle concentration) the nanoparticles can be charged. Both the polarity and magnitude of the surface charge are found to depend strongly on the acid-base properties of the surface and the surfactant.

SUMMARY

A facile method is provided for stabilizing nanoparticles in nonpolar solvents. The method involves using an ion complex of an acid and a base to stabilize nanoparticles, including bare nanoparticles that do not have any covalently bonded surface molecules. The ions are selected to have a mutual solubility in the targeted nonpolar solvent to act as a bridge between the nanoparticles and the solvent. The method involves using two different molecules: cation and anion, where at least one of them is soluble with the target nonpolar solvent and the other one has strong affinity for the surface of the nanoparticles. Both molecules, the cation and the anion, together form a cluster of ion pairs shielding the nanoparticles and enhancing their dispersibility on the target nonpolar solvent. In this way, interactions between the surface of the nanoparticles and surface-associated ion pairs provides a degree of stabilization.

DETAILED DESCRIPTION

Figure 1:
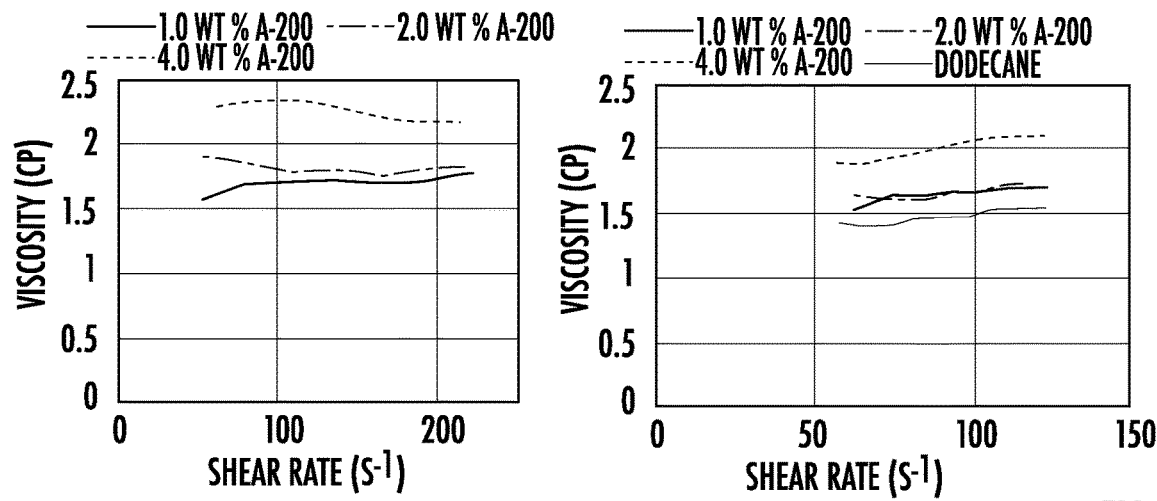
FIG. 1 includes two line graphs, illustrating the results of viscosity measurements of samples 58, 59, and 60 with 1.0 wt % of IL2 and various wt % of Aerosil-200 (58—1.0, 59—2.0, 60—4.0) after sonication (left) and after 1 week (right).

One general aspect of the methods disclosed herein includes a method for stabilizing a dispersion of nanoparticles in a nonpolar solvent, including admixing with the nanoparticles in the solvent stabilizing amounts of an anionic species and a cationic species that together form ionic or hydrogen bonds therebetween in the dispersion, where a first one of the anionic or the cationic species has a higher relative affinity for the nanoparticles in the solvent, and the other of the anionic or cationic species has a greater relative solubility in the nonpolar solvent than the first ionic species. The method also includes where the cationic species and the anionic species are each separately soluble in the non-polar solvent in the stabilizing amounts, or the anionic and cationic species are together capable of forming an ionic compound that is soluble in the non-polar solvent to provide the anionic and cationic species in the stabilizing amounts; and. The method also includes where the dispersion is formed into a stable non-precipitating dispersion of the nanoparticles in the presence of the anionic and cationic species in the nonpolar solvent, under stabilized conditions for a stabilized period of time where, in the absence of the anionic and the cationic species, the nanoparticles would precipitate under the stabilized conditions within the stabilized period of time.

Implementations may include one or more of the following features. The method where the ionic compound is an ionic liquid at a temperature at which the dispersion is stabilized, or under the stabilized conditions. The method where the ionic liquid has a melting point below 200° C. The method where the ionic liquid includes a primary, secondary, tertiary or cyclic amine. The method where the ionic liquid includes a primary, secondary or tertiary alkyl amine. The method where the ionic liquid includes one or more primary carboxylic acid, saturated or unsaturated. The method where the ionic liquid includes one or more primary sulfonic acid, saturated or unsaturated, such as an alkyl sulfonic acid. The method where the ionic liquid includes one or more primary, saturated or unsaturated alkyl benzene sulfonic acid. The method where the ionic liquid is butylammonium oleate, N-octylammonium oleate, tri-ethylammonium oleate, tri-N-butylammonium oleate, or tri-N-octylammonium oleate, butylammonium dodecyl benzenesulfonate, n-octylammonium dodecyl benzenesulfonate, tri-ethylammonium dodecyl benzenesulfonate, tri-n-butylammonium dodecyl benzenesulfonate, tri-n-octylammonium dodecyl benzenesulfonate. The method where the nonpolar solvent has a dielectric constant of less than 15. The method where the stabilized conditions include an average or maximum gravitational force during the stabilized period of 1 gravity and an ambient temperature or a temperature above a freezing point or below a boiling point of the dispersion. The method where the nanoparticles include a nanoparticle is included substantially of a metal, a metalloid, a metal oxide, a metalloid oxide, carbon, cellulose or a mixture thereof. The method where the metal or metaloid oxide includes silicon oxide, iron oxide or aluminium oxide; the carbon includes carbon black or carbon nanotubes; or, the cellulose includes cellulose nanocrystals. The method where the nanoparticles include a nanoparticle including an element selected from the group including of Fe, Al, Ag, Au, Co, Mo, N, Ni, Pd, Pt, S, Sn, Si, Ti, W, or Zn. The method where the nanoparticles have an average dimension ranging from 1 nm to 1000 nm. The method where the nanoparticles include a nanoparticle that has a charged particle surface in the dispersion. The method where the charged surface is positively charged. The method where the charged surface is negatively charged. The method where the nanoparticles include a nanoparticle that does not have a charged particle surface in the dispersion. The method where the stabilization period is 1 day, 1 week, 1 month or 1 year. The method where the nanoparticles are present in the dispersion in an amount ranging from 0.0001 wt. % to 50 wt. % relative to the dispersion weight (for example being greater than 0.0001 wt. %, 0.001 wt. %, 0.01 wt. %, 0.1 wt. %, 1 wt. %, 10 wt. %, 20 wt. %, or 30 wt. % and/or less than 50 wt. %, 40 wt. %, 30 wt. %, 20 wt. %, 10 wt. %, 1 wt. %, 0.1 wt. % or 0.01 wt. %, or any range between any two of these lower and upper amounts). The method where a weight ratio of the combined anionic and cationic species to the nanoparticles in the dispersion ranges from 1:10 to 10:1 combined species to nanoparticles (for example being about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1 or 10:1, or in any range between any two of these ratios). The stable non-precipitating dispersion of the nanoparticles in the presence of the anionic and cationic species in the nonpolar solvent, made according to the method.

One general aspect includes a stable dispersion of nanoparticles in the presence of anionic species and cationic species in a nonpolar solvent, where the anionic and cationic species are present in solvent stabilizing amounts and together form ionic or hydrogen bonds therebetween in the dispersion, where a first one of the anionic or the cationic species has a higher relative affinity for the nanoparticles in the solvent, and the other of the anionic or cationic species has a greater relative solubility in the nonpolar solvent than the first ionic species. The stable dispersion of nanoparticles also includes where the cationic species and the anionic species are each separately soluble in the non-polar solvent in the stabilizing amounts, or the anionic and cationic species are together capable of forming an ionic compound that is soluble in the non-polar solvent to provide the anionic and cationic species in the stabilizing amounts; and. The stable dispersion of nanoparticles also includes where the stable dispersion is non-precipitating under stabilized conditions for a stabilized period of time where, in the absence of the anionic and the cationic species, the nanoparticles would precipitate under the stabilized conditions within the stabilized period of time.

Aspects of the disclosed processes include processes having a single stabilization step that provides a stable dispersion, with no solvent transfer, heat or complex chemical reactions required. These ADL methods may accordingly be adapted for applications such as: water-in-oil emulsions in the food industry; water-in-oil emulsions for drilling fluids; nonaqueous foams; dispersion of Graphene oxides; liquid immersion development (LID); electrostatic lithography; drop-on-demand ink jet; photoelectrophoresis; electrophoretic displays; or electrorheological fluids.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

EXAMPLES

The following Example relate generally to the formation of stable dispersions in non-aqueous liquid medium of nanoparticles such as carbon-based nanoparticles, inorganic nanoparticles, and organic nanoparticles by direct addition of the nanoparticles and the ionic liquid stabilizer to the desired solvent.

Materials and Methods

N-decylamine, N-butylamine, N-octylamine, tri-N-butylamine, tri-N-octylamine, and N,N'-Dimethyl-1,3-propanediamine were purchased from TCI chemicals. Iso stearic acid was obtained from TCI chemicals. Oleic acid was obtained as a technical grade. All the chemicals were used without further purification.

Ionic Liquids (Ls) were synthesized using the procedure discussed elsewhere (McCrary et al. 2013). ILs were synthesized first by mixing the bulk base and acid. While acid-base solutions (Abs) were made by directly adding the acid and base in any order into the nonpolar solvents. The molar ratio of the base-to-acid is 10:1, 5:1, 1:1, 1:5, or 10:1.

Three different oxide nanoparticles were used. Aerosil-200 Fumed silica and Aeroxide Alu C nanoparticles were purchased from Evonik. Iron oxide nanoparticles were obtained from SkySpring. The nanoparticles were in powder form. Carbon black (Vulcan-XC-72R), non-oxide nanoparticles, was obtained from Cabot. Carbon nanotubes were obtained from Cheap Tubes Inc.

TABLE 1

Structure of ionic liquids used in this study

| # | Full Name | Chemical Formula |
|---|---|---|
| IL1 | Butylammonium oleate | [$C_4NH_3$][oleate] |
| IL2 | N-octylammonium oleate | [$C_8NH_3$][oleate] |
| IL3 | N-dodecylammonium oleate | [$C_{12}NH_3$][Oleate] |
| IL4 | Tri-ethylammonium oleate | [$HN_{222}$][oleate] |
| IL5 | Tri-N-butylammonium oleate | [$HN_{444}$][oleate] |
| IL6 | Tri-N-octylammonium oleate | [$HN_{888}$][oleate] |
| IL7 | N-octylammonium dodecyl benzenesulfonate | [$C_8NH_3$][DBS] |
| AB1 | N-octylamine/oleic acid(1:1M) | |
| AB2 | N,N'-Dimethyl-1,3-propanediamine/Iso-Stearic acid (1:1M) | |

In order to stabilize the nanoparticles in nonpolar solvents, these examples illustrate a variety of embodiments that make use of different acids, bases, and mixtures of acids and bases, in the form of either ILs or ABs. The ILs were diluted in the nonpolar organic solvents. In case of ABs, the acid and base were added individually and directly to the nonpolar organic solvents. Moreover, the acid and base were tested individually and tested for their efficiency of stabilized bare nanoparticles in nonpolar organic solvents. Then the nanoparticles were added, and the solutions were sonicated for 2 minutes using ultrasonication probe. The following procedure was used to prepare the nanoparticles dispersions in nonpolar solvents.

A mixture of dodecane (in some case, N-Hexane was used) with a specified wt % of the reagent was stirred for 30 minutes (500-700 rpm) with a magnetic stirrer. A funnel was used to add nanoparticles to the solution while stirring at high speed (1000 rpm). The stir bar used was small and flat in order to avoid the formation of a vortex at the meniscus of the solution which could cause particles to shoot up and collect on the edges of the vial. The mixture was then sonicated for 2 minutes (30 sec. on, 30 sec off) with an ultrasonication probe (420-A micro-tip) at 50% amplitude. The vial was grounded in an ice bath during sonication.

Photographs of the samples were taken, and visual observations were recorded at different time intervals. The particle size distribution (PSD) was measured using DLS with glass cuvette at different time intervals. Viscosity was measured using concentric cylinders viscometer (16 mL cylinder holder with ULA spindle). Particle size distribution of the nanoparticles was then measured using dynamic light scattering (DLS) with NanoPlus HD instrument. Viscosity measurements were conducted using Brookfield DV2T viscometer. ICP-MS triple quad was used to determine the concentration of iron oxide in the supernatants. The $Fe_3O_4$ was first digested using nitric acid at 90° C. before injecting it into the ICP-MS.

Results and Discussions

Dispersion of Aerosil-200 Fumed Silica Nanoparticles in Dodecane

Acids

In this section, two different organic acids; oleic acid and iso-stearic acids were tested for their effect on bare silica nanoparticles stability in dodecane. Aerosil-200 Fumed Silica nanoparticles dispersions in dodecane without organic acids are unstable.

Without addition of any stabilizer, at low concentrations of nanoparticles (1-2 wt %), flocculation was observed immediately after sonication. While at higher concentrations of nanoparticles (4-8 wt %), gelation was produced either during stirring (4 wt %) or during sonication (8 wt %).

With the addition of oleic acid or iso-stearic acids, at low concentrations of nanoparticles, stability was improved slightly for the first 2-3 hours. However, flocculation developed heavily afterwards. Samples with higher concentrations of nanoparticles also formed gels. Samples with 4 and 8 wt % nanoparticles gelled during stirring and sonication, respectively.

Table 2 shows the composition of the samples that were prepared, and their characterization based on visual observation after sonication and after 1 week of preparation.

TABLE 2

Effect of acids on the stability of nanoparticles in dodecane (After sonication)

| # | Reagent | Reagent wt % | Aerosil-200, wt % | Dodecane wt % | Visual Observation After sonication | After 1 week |
|---|---|---|---|---|---|---|
| DB46 | None | 0 | 1.0 | 99.0 | Immediate Flocculation | Remained flocculated |
| DB47 | None | 0 | 2.0 | 98.0 | Immediate Flocculation | |
| DB48 | None | 0 | 4.0 | 96.0 | Gelling (sonication) | Remained Gelled |
| DB49 | None | 0 | 8.0 | 92.0 | Gelling (stirring) | Remained Gelled |
| DB50 | Oleic Acid | 1 | 1.0 | 98.0 | Flocculation within 2-3 h | Precipitated |

TABLE 2-continued

Effect of acids on the stability of nanoparticles in dodecane (After sonication)

| # | Reagent | Reagent wt % | Aerosil-200, wt % | Dodecane wt % | Visual Observation After sonication | After 1 week |
|---|---|---|---|---|---|---|
| DB51 | Oleic Acid | 1 | 2.0 | 97.0 | Immediate Flocculation | Precipitated |
| DB52 | Oleic Acid | 1 | 4.0 | 95.0 | Gelling (sonication) | Remained Gelled |
| DB53 | Oleic Acid | 1 | 8.0 | 91.0 | Gelling (stirring) | Remained Gelled |
| DB54 | Iso-stearic Acid | 1 | 1.0 | 98.0 | Flocculation 2-3 hrs | Precipitated |
| DB55 | Iso-stearic Acid | 1 | 2.0 | 97.0 | Flocculation 2-3 hrs | Remained flocculated |
| DB56 | Iso-stearic Acid | 1 | 4.0 | 95.0 | Gelling (sonication) | Remained Gelled |
| DB57 | Iso-stearic Acid | 1 | 8.0 | 91.0 | Gelling (stirring) | Remained Gelled |

The particles size distribution (PSD) measurements were performed on the samples presented in Table 2 right after sonication and the PSD measurements repeated after 1 week, to assess cumulative diameter and Polydispersity Index (PDI). As shown below in Table 3, heavy flocculation was attained in all the samples. These experiments show that a variety of organics acids cannot stabilize silica nanoparticles in dodecane.

TABLE 3

PSD parameters for non-flocculated and non-gelled samples containing 1.0 wt % of reagents (Oleic Acid, Iso-stearic Acid) with various Aerosil-200 wt %.

| | | | | After sonication | | After 1 week | |
|---|---|---|---|---|---|---|---|
| Sample | Reagent | Reagent wt % | Aerosil-200 wt % | Cumulative Diameter (nm) | PDI | Cumulative Diameter (nm) | PDI |
| DB51 | Oleic Acid | 1 | 2.0 | 3887.1 | 1.784 | — | — |
| DB54 | Iso-stearic Acid | 1 | 1.0 | 2863.7 | 1.754 | — | — |
| DB55 | Iso-stearic Acid | 1 | 2.0 | 8738.3 | 2.54 | — | — |

Bases

In order to evaluate the effect of organic bases on the stability of nanoparticles in nonpolar solvents, two organic bases were tested. In this section, N-octylamine and N, N'-Dimethyl-1, 3-propanediamine were mixed with Aerosil-200 Fumed silica nanoparticles using the procedure explained previously. N-octylamine did not stabilize the nanoparticles in dodecane. While N-octylammonium acetate was not miscible in dodecane at ambient temperature. N, N'-Dimethyl-1, 3-propanediamine had similar performance to N-octylamine. As shown in Table 2, none of the bases tested could achieve long-term stability of the Aerosil-200 Fumed Silica nanoparticles dispersion in dodecane. However, the nanoparticles are more stable compared to the one without stabilizers or with acids.

Table 4 shows the compositions of the samples tested in this section and their visual observation after sonications. As shown in the table, N, N'-Dimethyl-1,3-propanediamine is slightly efficient compared to N-octylamine.

The particles size distribution (PSD) measurements were performed on the sample with N-octylamine right after sonication. Heavy flocculation was attained in the sample. Table 5 shows the sonication and PSD parameters for samples containing various Octylamine at 1.0 wt % with 1 wt % Aerosil-200 wt %.

TABLE 4

Effect of bases on the stability of nanoparticles in dodecane (After sonication)

| Sample Name | Reagent | Reagent wt % | Aerosil-200, wt % | Dodecane wt % | Visual Observation |
|---|---|---|---|---|---|
| DB124 | N-octylamine | 1 | 1.0 | 98 | Immediate Flocculation |
| DB131 | N-octylammonium Acetate | 1 | N/A | 98 | insoluble |
| | N,N'-Dimethyl-1,3-propanediamine | 1 | 0.1 | 98.9 | Flocculation 2-3 hrs |
| | N,N'-Dimethyl-1,3-propanediamine | 1 | 0.25 | 98.75 | Flocculation 2-3 hrs |

TABLE 5

Sonication and PSD parameters for samples containing various Octylamine at 1.0 wt % with 1 wt % Aerosil-200 wt %.

| Sample | Reagent | Reagent wt % | Aerosil-200 wt % | Energy Input (J) | Cumulative Diameter (nm) | PDI |
|---|---|---|---|---|---|---|
| 124 | Octylamine | 1 | 1 | 3496 | 2375.9 | 1.385 |

Ionic Liquids (ILs)

In order to illustrate the present Artificial Double Layer (ADL) approach, several ILs were synthesized using the protocols referenced herein, and tested as follows. ILs of primary and tertiary amines combined with oleic acid were tested. The acids and bases for these ILs were tested in the previous sub-sections, and none of them could stabilize Aerosil-200 Fumed Silica nanoparticles in dodecane.

However, primary amine-based ILs were able to stabilize Aerosil-200 Fumed Silica nanoparticles for long term. With 1 wt % of IL2, stable dispersions of Aerosil-200 Fumed Silica nanoparticles at concentrations of 1, 2, and 4 wt %. While for 6 and 8 wt % of Aerosil-200 Fumed Silica nanoparticles, the dispersion gelled during stirring or sonication. IL1 and IL3 with primary amine of shorter and longer alkyl chain, respectively, could stabilize the dispersions and gave similar performance to IL1.

IL5 and IL6 with tertiary amines were barely able to stabilize the dispersion for 2-3 hrs when heavy flocculation and separation of nanoparticles started. Even the samples with IL5 and IL6 formed gel during sonication at lower concentration of Aerosil-200 Fumed Silica nanoparticles (4 wt %) compared to 6 wt % of Aerosil-200 Fumed Silica nanoparticles in the presence of primary amine-based ILs.

It is concluded that the formation of ion pairs is more efficient in the case of primary-amines due to the availability of 2 hydrogen atoms attached to the highly electronegative nitrogen. Hence, primary amines can form an H-bond with themselves and with the acid, giving a more complex clusters of ions. While tertiary amines can form an H-bond only with the acid by sharing the lone pair of electrons on the highly electronegative nitrogen. Due to the absence of a hydrogen atom attached to the nitrogen, tertiary amines can't form hydrogen bonds with themselves.

Table 5 summarizes the composition of the samples prepared with different ILs and the visual observation of these samples after sonication and after 1 week. Samples containing 1.0 wt % IL1, IL2 or IL3 were the only sample to not gel during sonication at 4.0 wt % of Aerosil-200. All samples gelled at 8.0 wt % and had bubbles trapped in the gel, with the control and Oleic Acid samples containing the most air bubbles. Both IL5 and IL6 samples at 1.0 wt % and 2.0 wt % had the Aerosil-200 falling out of solution by the end of the day, however, the IL5 samples (64 and 66) seemed to be separating at a faster rate than the IL4 samples.

TABLE 5

Screening of different ILs for their stabilization of nanoparticles in dodecane after sonication and after 1 week.

| Sample Name | Reagent | Reagent wt % | Aerosil-200 wt % | Dodecane wt % | Visual Observation After Sonication | After 1 Week | |
|---|---|---|---|---|---|---|---|
| DB58 | IL2 | 1 | 1.0 | 98.0 | Dispersed | Remained Dispersed | Translucent |
| DB59 | IL2 | 1 | 2.0 | 97.0 | Dispersed | Remained Dispersed | Translucent-Cloudy |
| DB60 | IL2 | 1 | 4.0 | 95.0 | Dispersed | Remained Dispersed | Cloud |
| DB132 | IL2 | 1 | 6.0 | 93.0 | Gelled while stirring | Remained Gelled | Opaque |
| DB61 | IL2 | 1 | 8.0 | 91.0 | Gelled during sonication | Remained Gelled | Opaque |
| DB125 | IL2 | 2 | 8.0 | 90 | Gelled during sonication | Remained Gelled | Opaque |
| DB122 | IL1 | 1 | 1.0 | 98 | Dispersed | Remained dispersed | Translucent |
| DB127 | IL1 | 1 | 2.0 | 97 | Dispersed | Remained dispersed | Translucent-Cloudy |
| DB128 | IL1 | 1 | 4.0 | 95 | Dispersed | Remained dispersed | Cloud |
| DB133 | IL1 | 1 | 6.0 | 93 | Gelled during sonication | Remained Gelled | Opaque |
| DB123 | IL3 | 1 | 1.0 | 98 | Dispersed | Remained dispersed | Translucent |
| DB129 | IL3 | 1 | 2.0 | 97 | Dispersed | Remained dispersed | Translucent-Cloudy |
| DB130 | IL3 | 1 | 4.0 | 95 | Dispersed | Remained dispersed | Cloud |
| DB134 | IL3 | 1 | 6.0 | 93 | Gelled during sonication | Remained Gelled | Opaque |
| DB62 | IL5 | 1 | 1.0 | 98.0 | Flocculation 2-3 hrs | Precipitated | |
| DB63 | IL5 | 1 | 2.0 | 97.0 | Flocculation 2-3 hrs | Precipitated | |
| DB64 | IL5 | 1 | 4.0 | 95.0 | Gelled during sonication | Remained Gelled | Opaque |
| DB65 | IL5 | 1 | 8.0 | 91.0 | Gelled while stirring | Remained Gelled | Opaque |
| DB66 | IL6 | 1 | 1.0 | 98.0 | Flocculation 2-3 hrs | Precipitated | |
| DB67 | IL6 | 1 | 2.0 | 97.0 | Flocculation 2-3 hrs | Precipitated | |
| DB68 | IL6 | 1 | 4.0 | 95.0 | Gelled during sonication | Remained Gelled | Opaque |
| DB69 | IL6 | 1 | 8.0 | 91.0 | Gelled while stirring | Remained Gelled | Opaque |

Although the diameter and PDI of the IL6 samples (66 and 67) indicates that they would be more stable than the IL5 samples (62 and 63), visual observation of precipitation do not agree. The phase separation may be due to the increased hydrophobicity of IL6 compared to IL5 due to base alkyl chain length. The base may be more prone to the organic phase and is not interaction through H-bonding with silanol groups on Aerosil-200, resulting in a separation of two phases: organic phase with dodecane and IL, and Aerosil-200 as precipitate.

New samples were prepared to test the dispersion of IL5 and IL6 at 1.0 and 2.0 wt % of Aerosil-200. These specific concentrations saw precipitation of the Aerosil-200 hours after sonication on the day of their preparation. Although PSD measurements of these samples align with previous trials done with IL5 and IL6 using 1.0 wt % of Aerosil-200, a previous trial done with IL5 and 1.0 wt % Aerosil-200 did not begin to separate until till after 10 days. The following samples were prepared:

TABLE 6

Composition of repeated IL4 and IL5 samples

| Sample Name | Reagent (1.0 wt %) | Aerosil-200 wt % | Dodecane wt % |
|---|---|---|---|
| DB70 | IL5 | 1.0 | 98.0 |
| DB71 | IL5 | 2.0 | 97.0 |
| DB72 | IL6 | 1.0 | 98.0 |
| DB73 | IL6 | 2.0 | 97.0 |

These samples also saw quick separation due to precipitation hours after initial sonication, and pictures were retaken 24 hours after sonication. The IL6 samples experiences much more rapid separation as compared to the IL5 samples. The cumulative diameter and larger PDI of the IL6 samples compared to the IL5 samples agrees with the faster separation that was observed after 24 hours. The following are PSD measurements that were taken immediately after sonication.

TABLE 7

Visual observations of repeated IL5 and IL6 samples

| Sample | Reagent | Reagent wt % | Aerosil-200 wt % | Dodecane wt % | Visual Observation |
|---|---|---|---|---|---|
| DB70 | IL5 | 1 | 1.0 | 98 | Phase Separated, Clear Upper, Opaque Bottom |
| DB71 | IL5 | 1 | 2.0 | 98 | Phase Separated, Clear Upper, Opaque Bottom |
| DB72 | IL6 | 1 | 1.0 | 98 | Phase Separated, Clear Upper, Opaque Bottom |
| DB73 | IL6 | 1 | 2.0 | 98 | Phase Separated, Clear Upper, Opaque Bottom |

PSD results were also obtained for many samples, but some samples were too heavily flocculated or gelled to obtain reliable results. Table 8 shows the PSD parameters of ILs samples with Aerosil-200 after sonication and after 1 week.

TABLE 8

PSD parameters of ILs samples with Aerosil-200 after sonication and after 1 week.

| Sample | Reagent | Reagent wt % | Aerosil-200 Concentration (wt %) | After sonication Cumulative Diameter (nm) | After sonication PDI | After 1 week Cumulative Diameter (nm) | After 1 week PDI |
|---|---|---|---|---|---|---|---|
| DB58 | IL1 | 1 | 1.0 | 194.9 | 0.105 | 189.5 | 0.093 |
| DB59 | IL1 | 1 | 2.0 | 210.1 | 0.147 | 209.7 | 0.128 |
| DB60 | IL2 | 1 | 4.0 | 222.5 | 0.157 | 218.7 | 0.158 |
| DB132 | IL2 | 1 | 6.0 | — | — | — | — |
| DB61 | IL2 | 1 | 8.0 | — | — | — | — |
| DB125 | IL2 | 2 | 8.0 | — | — | — | — |
| DB122 | IL1 | 1 | 1.0 | 204.5 | 0.131 | 205.4 | 0.139 |
| DB127 | IL1 | 1 | 2.0 | 222.9 | 0.186 | 210.9 | 0.128 |
| DB128 | IL1 | 1 | 4.0 | 233.6 | 0.192 | 232.2 | 0.171 |
| DB133 | IL1 | 1 | 6.0 | — | — | — | — |
| DB123 | IL3 | 1 | 1.0 | 204.2 | 0.142 | 196.5 | 0.139 |
| DB129 | IL3 | 1 | 2.0 | 198.4 | 0.16 | 207.5 | 0.166 |
| DB130 | IL3 | 1 | 4.0 | 230.9 | 0.168 | 224.6 | 0.163 |
| DB134 | IL3 | 1 | 6.0 | — | — | — | — |
| DB70 | IL5 | 1 | 1.0 | 927.4 | 0.585 | — | — |
| DB71 | IL5 | 1 | 2.0 | 1154 | 0.721 | — | — |
| DB64 | IL5 | 1 | 4.0 | — | — | — | — |
| DB65 | IL5 | 1 | 8.0 | — | — | — | — |
| DB72 | IL6 | 1 | 1.0 | 742.1 | 0.496 | — | — |
| DB73 | IL6 | 1 | 2.0 | 591.9 | 0.427 | — | — |
| DB68 | IL6 | 1 | 4.0 | — | — | — | — |
| DB69 | IL6 | 1 | 8.0 | — | — | — | — |

Viscosity measurements were also conducted. However, their validity needs to be re-assessed, and a suitable control needs to be decided. The control samples with only Aerosil-200 had a very low sample recovery from the viscometer due to the previously mention viscous fluid on the walls of the vials. Dodecane itself may serve as a better control test for viscosity.

Viscosity measurement of the IL2 samples indicate that the samples remained Newtonian after one week (FIG. 1). For the measurements, a 16 mL cylinder was used with a ULA spindle, and all measurements had torque between 10-100% with minimum speeds ranging from 40-50 rpm and the maximum speed set at 100 rpm for all samples.

Figure 2:
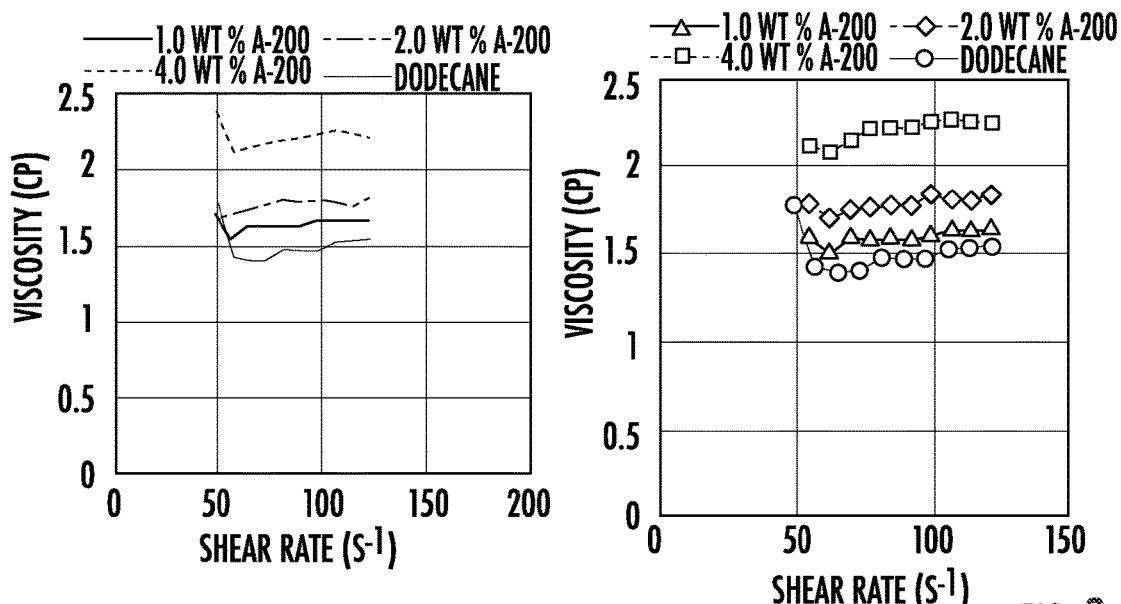
FIG. 2 includes two line graphs, illustrating the results of viscosity measurements of samples 122, 127, and 128 with 1.0 wt % IL1 and different wt % of Aerosil-200 (122—1.0, 127—2.0, 128—3.0), (left) after sonication, and (right) after 1 week.
Figure 3:
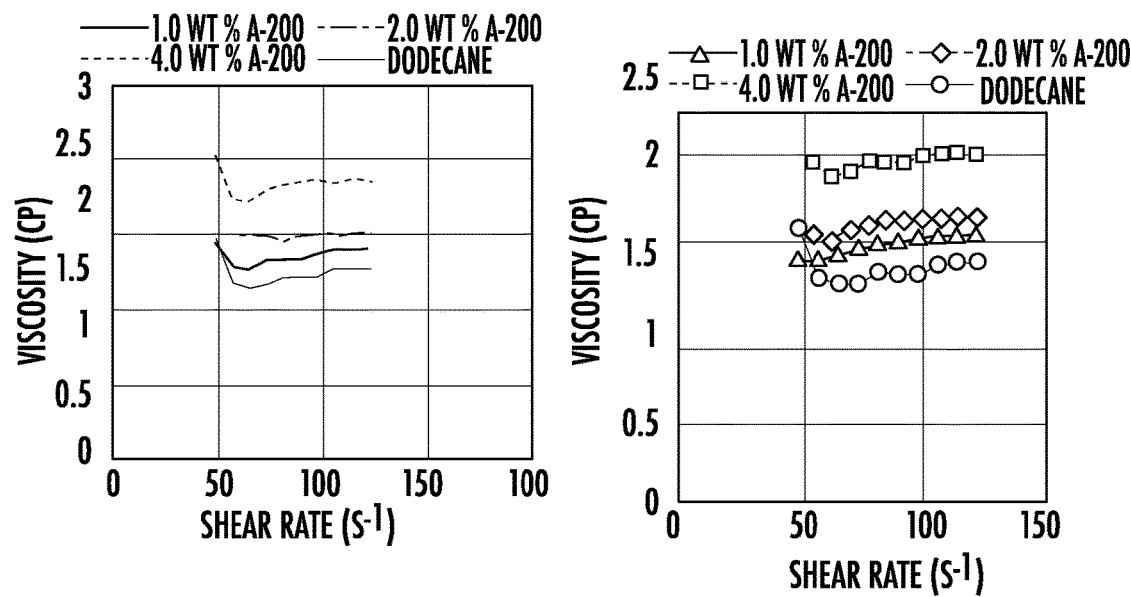
FIG. 3 includes two line graphs, illustrating the results of viscosity measurements of samples 123, 129, and 130 with 1.0 wt % IL3 and different wt % of Aerosil-200 (123—1.0, 129—2.0, 130—3.0), (left) after sonication, and (right) after 1 week.

Viscosity measurements were taken for all the IL1 and IL3 samples using a 16 mL cylinder and ULA spindle. All measurements were taken using RPM's ranging from 40-100, all between 10-100% torque Increases in viscosity for samples using IL1 were greater for 1.0, 2.0, and 4.0 wt % Aerosil-200 compared to sample made using IL1 or IL3 from this week. However, viscosity increases IL1 and IL3 were almost identical at all well-dispersed concentrations of Aerosil-200 as seen in FIGS. 2 and 3.

Figure 4:
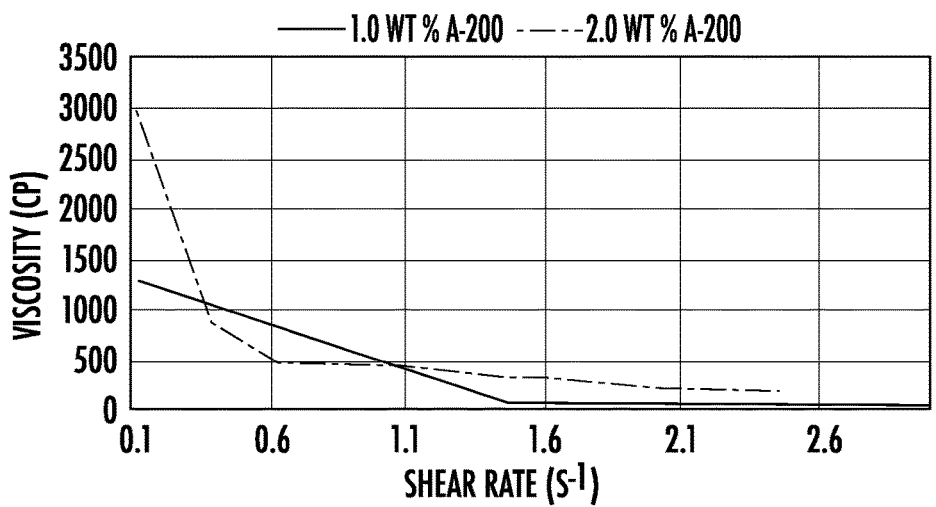
FIG. 4 is a line graph, illustrating the results of viscosity measurements of samples 62 (1.0 wt % Aeroil-200) and 63 (2.0 wt % Aeroil-200), both with 1.0 wt % of IL5.

FIG. 4 shows the Viscosity measurements of samples 62 (1.0 wt % Aeroil-200) and 63 (2.0 wt % Aeroil-200), both with 1.0 wt % of IL5. As shown the samples are highly viscous and shear thinning indicating the growth of nanoparticles structures in the solutions High Concentration of IL2

Previously, 8.0 wt % Aerosil-200 Fumed Silica nanoparticles in solution formed gels for all samples containing IL1, IL2, and IL3. Therefore, samples with a higher weight ratio between IL2 and dodecane were prepared to see if it was possible to disperse 8.0 wt % Aerosil-200 Fumed Silica nanoparticles without gelation. All higher concentration (>10 wt % of IL2) were able to stabilize the Aerosil-200 Fumed Silica nanoparticles and the condition of samples prepared are summarized below (Table 9).

TABLE 9

Weight fractions and state of samples 138-143 after sonication and after 1 week.

| Sample Name | Reagent | Weight Fraction of IL1:Dodecane | Aerosil-200 wt % in Dodecane-IL mixture | Visual Observation After sonication | After 1 Week |
|---|---|---|---|---|---|
| DB140 | IL2 | 10:90 | 8.0 | Dispersed | Remained dispersed |
| DB141 | IL2 | 20:80 | 8.0 | Dispersed | Remained dispersed |
| DB142 | IL2 | 30:70 | 8.0 | Dispersed | Remained dispersed |
| DB143 | IL2 | 40:60 | 8.0 | Dispersed | Remained dispersed |
| DB138 | IL2 | 50:50 | 8.0 | Dispersed | Remained dispersed |
| DB139 | IL2 | 50:50 | 8.0 | Dispersed | Remained dispersed |

The PSD for samples 140, 141, and 142 (10:90, 20:80, and 30:70 of IL2:dodecane, respectively) which all contained 8.0 wt % Aerosil-200 displayed two peaks in their distributions. The first peak centered on a smaller diameter (<100 nm) for all three of these samples did not make up a significant part of either the intensity or volume distributions but had a larger percentage of the number distributions. Sample 143 (40:60 of IL2:dodecane), also containing 8.0 wt % Aerosil-200, did not display this behavior with its PSD as it only had a single peak. The peaks in the range <100 nm more likely belongs to the micelles of IL2. In comparison to the PSD measured after sonication, samples 140-142 did not display the secondary peaks seen in the intensity, volume, and number distributions after 1 week. The PDI and cumulative diameter also indicate smaller hydrodynamic diameters and more monodisperse particles after 1 week. Table 10 shows the sonication and PSD parameters for samples 140-143 containing 8.0 wt % Aerosil-200 with different ratios of IL2:dodecane after sonication and after 1 week.

TABLE 10

Sonication and PSD parameters for samples 140-143 containing 8.0 wt % Aerosil-200 with different ratios of IL1:dodecane after sonication and after 1 week.

| | | | After sonication | | After 1 Week | |
|---|---|---|---|---|---|---|
| Sample | Weight Fraction of IL2:Dodecane | Energy Input (J) | Cumulative Diameter (nm) | PDI | Cumulative Diameter (nm) | PDI |
| 140 | 10:90 | 4089 | 224.5 | 0.16 | 197.1 | 0.147 |
| 141 | 20:80 | 3918 | 276.6 | 0.173 | 216.5 | 0.11 |
| 142 | 30:70 | 4241 | 282 | 0.192 | 235.9 | 0.132 |
| 143 | 40:60 | 4353 | 237.4 | 0.121 | 198.3 | 0.162 |

In order to elucidate the micelles of IL2, PSD results were gathered for samples with only IL2 and dodecane with the same weight fractions used for samples 140-143. The samples were sonicated for 2 minutes consistent with samples 140-143. Table 11 shows the sonication and PSD parameters for samples 144-147 containing different ratios of IL2:dodecane. The PSD clearly displayed some micelle formations. The intensity distribution for samples 144-147 (10:90, 20:80, and 30:70 weight fraction of IL:dodecane, respectively) all followed similar trends with multiple peaks ranging from 100 nm to 100000 nm for the intensity distributions. However, only single peaks were seen for the volume distribution (around 40000 nm) and number distributions (around 20 nm). Once again, the 40:60 weight fraction of IL:dodecane (sample 147) was an outlier as it displayed no PSD peaks, indicating no micelle formation. Sample 143, which also had the same ratio of IL:dodecane as sample 147, did not display a secondary peak as seen in other samples.

TABLE 11

Sonication and PSD parameters for samples 144-147 containing different ratios of IL2:dodecane.

| Sample | Weight Fraction of IL2:Dodecane | Energy Input (J) | Cumulative Diameter (nm) | PDI |
|---|---|---|---|---|
| 144 | 10:90 | 3692 | 796.4 | 0.591 |
| 145 | 20:80 | 3662 | 3356.8 | 1.79 |
| 146 | 30:70 | 3982 | 1752 | 1.022 |
| 147 | 40:60 | 4022 | N/A | N/A |

Figure 5:
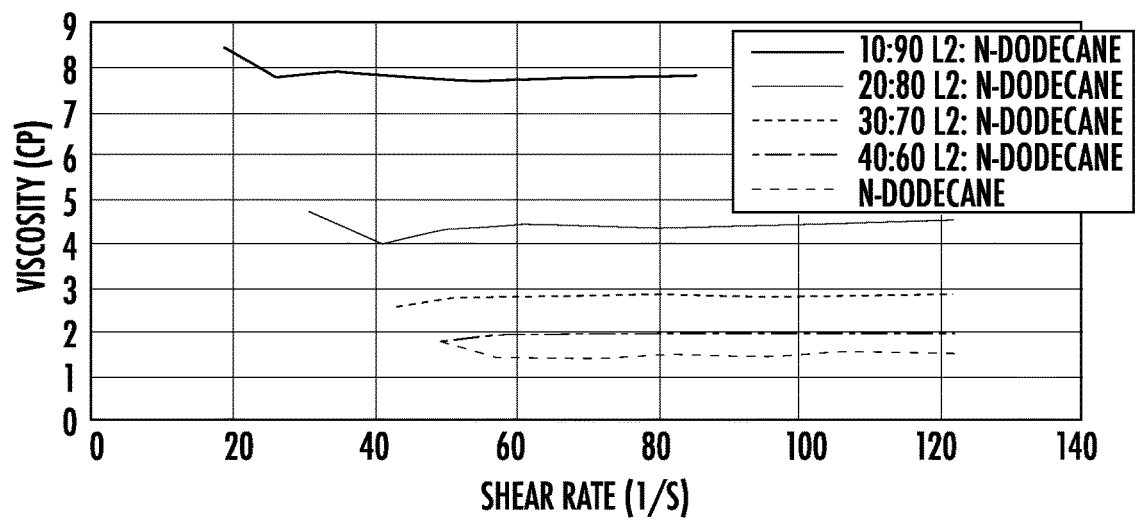
FIG. 5 is a line graph, illustrating the results of viscosity measurements of samples containing different ratios of IL2:dodecane (140—10:90, 141—20:80, 142—30:70, 143—40:60) prior to the addition of Aerosil-200.
Figure 6:
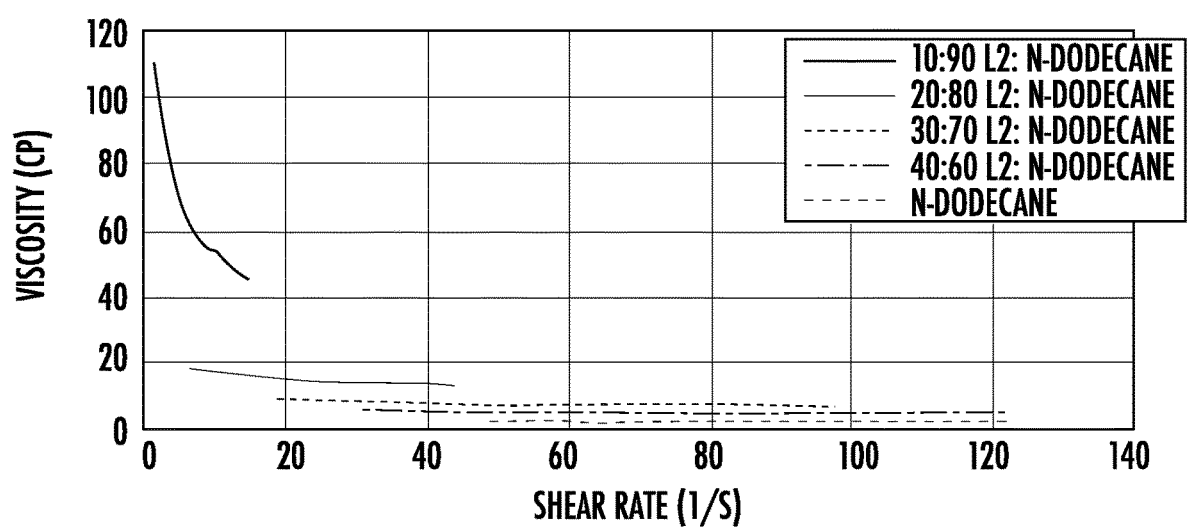
FIG. 6 is a line graph, illustrating the results of viscosity measurements of samples containing 8.0 wt % Aerosil-200 with different ratios of IL2:dodecane (140—10:90, 141—20:80, 142—30:70, 143—40:60) after sonication.
Figure 7:
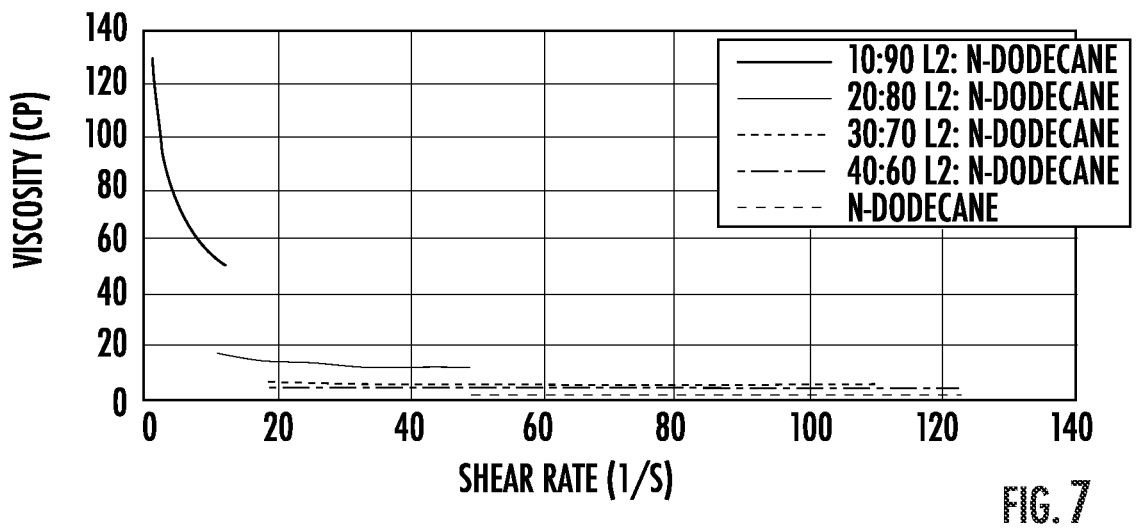
FIG. 7 is a line graph, illustrating the results of viscosity measurements of samples containing 8.0 wt % Aerosil-200 with different ratios of IL2:dodecane (140—10:90, 141—20:80, 142—30:70, 143—40:60) after 1 week.

Viscosity measurements for sample 140-143 were taken before and after the addition of Aerosil-200 as the concentration of IL2 was great enough in each sample to have an impact on the viscosity of the solution. The viscosity of the sample prior to the addition of NPs displayed a trend on increasing viscosity with increasing IL2 concentration and all samples had relatively constant viscosities with increasing shear rates (FIG. 5). However, after the addition of 8.0 wt % of Aerosil-200, each sample had a significant increase in viscosity, but also had slight shear thinning effects (FIG. 6). The degree of shear thinning increased with increasing concentration of IL2. Whether the samples are non-Newtonian or not will be summarized in next week's report by fitting the data to the power law. The viscosity of each samples 140-143 did not show significant change after 1 week and continue to be higher that dodecane or IL with dodecane alone (FIG. 7). The shear thinning effect observed in higher concentrations of IL2 are still seen. As the viscosity parameters for sample 140-143 were all greatly varying, they are summarized in Table 22. All viscosities were measured using a ULA spindle with a 16 mL holder and all torques ranged from 10-100%.

Acid-Base Solutions (ABs)

The ABs version of IL2 were also tested. The ABs of octylamine and oleic acid (1:1M) stabilized the nanoparticles dispersion as efficient as ILs.

Then the ABs of octylamine and oleic acid (1:1 M), AB1, was tested and compared to IL1. As shown in table 12, AB1 shows a good stability as IL2. Suggested that ABs can be replacing ILs. This makes the process much easier and more straightforward as no need for ILs synthesis since ABs in this case do the same job. Another acid-base solution was tested to validate the universality of the ADL theory. As shown in Table 12, AB2 can efficiently disperse Aerosil-200 Fumed silica nanoparticles in n-Hexane. While neither the diamine nor the iso-stearic acid can stabilize the dispersion.

Table 14 shows the sonication and PSD parameters for sample 135 and 136 containing 1.0 wt % of 1:1 M Octylamine and Oleic Acid and different Aerosil-200 wt %. AB1 can stabilize the dispersion up to 4 wt % of Aersolil-200. While 6 wt % of Aerosil-200 formed gel the same fashion as for IL2.

Figure 8:
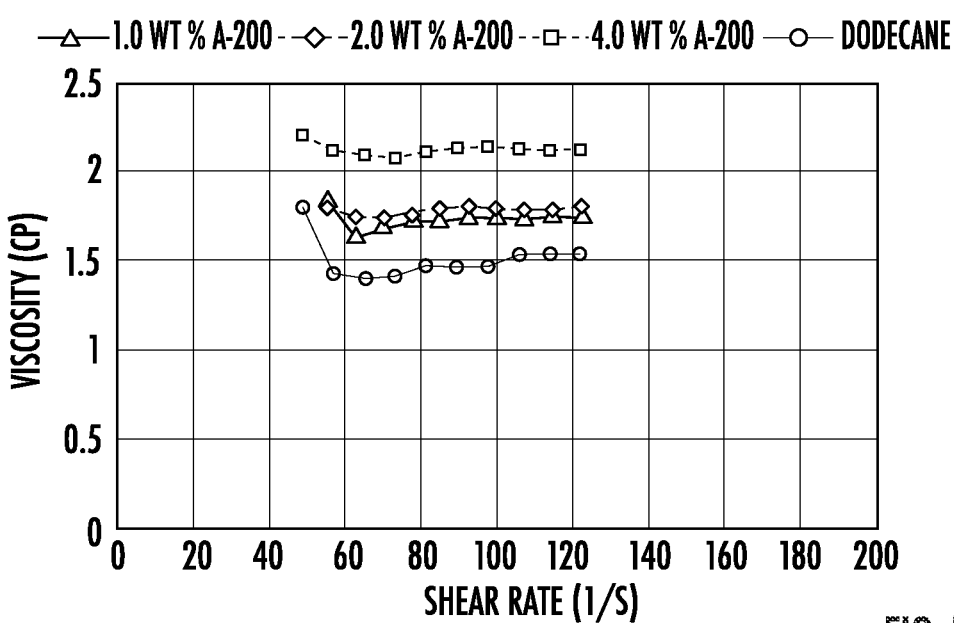
FIG. 8 is a line graph, illustrating the results of viscosity measurements of samples containing 1.0 wt % mixture of Octylamine and Oleic Acid (1:1 M) AB1 with different Aerosil-200 wt % (126—1.0 wt %, 135—2.0 wt %, and 136—4.0 wt %) after 1 week.

FIG. 8 shows viscosity measurements of samples containing 1.0 wt % mixture of Octylamine and Oleic Acid (1:1 M) AB1 with different Aerosil-200 wt % (126—1.0 wt %, 135—2.0 wt %, and 136—4.0 wt %) after 1 week. As shown, no significant increase in viscosity indicating a stable nanoparticles dispersion.

Hence, neither the acid nor base individually can achieve stability of the dispersion. However, when mixed together either the form of ILs or ABs, long term stability of the dispersion can be achieved. It's hypothesized that the ion pairs of acid and base can achieve the stability by creating an "Artificial Double Layer (ADL)" of mixed clusters of acid an bases with overall charges of either positive and negative.

Dispersion of SkySpring Iron Oxide in Dodecane

Ionic Liquids (ILs)

Previous trials showed the ability to effectively disperse up to 25% of $Fe_3O_4$ used after addition of IL5 and sonication for 1 hour with stability for over 3 months. The following procedure was run with different ILs (IL2, IL5 and IL6) at different concentrations (1.0, 2.0, 3.0, 4.0, and 5.0 wt %) as well as different sonication times (10 min, 30 min, and 1 hour):

Prepare a mixture of dodecane with a specified IL at various concentrations and stir for 30 minutes (anywhere from 500-700 rpm) with a magnetic stirrer;

Add 1 wt % of $Fe_3O_4$ to the solution and stir manually with a glass rod for 30 seconds;

Sonicate for various times (30 sec. on, 30 sec off) with a 408-B solid-tip at 50% amplitude in an ice bath;

Take pictures, and let sit for 24 hours to precipitate;

Recover supernatant after 24 hours; and,

Take pictures, and measure PSD and remaining $Fe_3O_4$ concentration in supernatant using ICP-MS.

Table 15 provides the summary of the samples tested for stability of ss-$Fe_3O_4$ in dodecane using ILs with the type analysis done for these samples.

TABLE 15

Summary of the samples tested for stability of ss-$Fe_3O_4$ in dodecane using ILs

| Sample Name | Sonication Time (min.) | IL Used | IL wt % | Dodecane wt % | Color Code |
|---|---|---|---|---|---|
| 74 | 10 | None | — | 99.0 | Samples with ICP-MS and PSD results |
| 75 | | IL2 | 1.0 | 98.0 | Samples with ICP-MS and PSD results |
| 76 | | IL2 | 2.0 | 97.0 | Samples with ICP-MS and PSD results |
| 77 | | IL2 | 3.0 | 96.0 | Samples with ICP-MS and PSD results |
| 78 | | IL2 | 4.0 | 95.0 | Samples with ICP-MS and PSD results |
| 79 | | IL2 | 5.0 | 94.0 | Samples with ICP-MS and PSD results |
| 80 | | IL5 | 1.0 | 98.0 | Samples with ICP-MS and PSD results |
| 81 | | IL5 | 2.0 | 97.0 | Samples with ICP-MS and PSD results |
| 82 | | IL5 | 3.0 | 96.0 | Samples with ICP-MS and PSD results |
| 83 | | IL5 | 4.0 | 95.0 | Samples with ICP-MS and PSD results |
| 84 | | IL5 | 5.0 | 94.0 | Samples with ICP-MS and PSD results |
| 85 | | IL6 | 1.0 | 98.0 | Samples with only PSD results which had to be diluted prior to DLS use |
| 86 | | IL6 | 2.0 | 97.0 | Samples with only PSD results which had to be diluted prior to DLS use |
| 87 | | IL6 | 3.0 | 96.0 | Samples with only PSD results which had to be diluted prior to DLS use |
| 88 | | IL6 | 4.0 | 95.0 | Samples with only PSD results which had to be diluted prior to DLS use |
| 89 | | IL6 | 5.0 | 94.0 | Samples with only PSD results which had to be diluted prior to DLS use |
| 90 | 30 | None | — | 99.0 | Samples with only PSD results which had to be diluted prior to DLS use |
| 91 | | IL2 | 1.0 | 98.0 | Samples with only PSD results which had to be diluted prior to DLS use |
| 92 | | IL2 | 2.0 | 97.0 | Samples with only PSD results which had to be diluted prior to DLS use |
| 93 | | IL2 | 3.0 | 96.0 | Samples with only PSD results which had to be diluted prior to DLS use |

TABLE 15-continued

Summary of the samples tested for stability of ss-Fe$_3$O$_4$ in dodecane using ILs

| Sample Name | Sonication Time (min.) | IL Used | IL wt % | Dodecane wt % | Color Code |
|---|---|---|---|---|---|
| 94 |  | IL2 | 4.0 | 95.0 | Samples with only PSD results which had to be diluted prior to DLS use |
| 95 |  | IL2 | 5.0 | 94.0 | Samples with only PSD results which had to be diluted prior to DLS use |
| 96 |  | IL5 | 1.0 | 98.0 | Samples with only PSD results which had to be diluted prior to DLS use |
| 97 |  | IL5 | 2.0 | 97.0 | Samples with only PSD results |
| 98 |  | IL5 | 3.0 | 96.0 | Samples with only PSD results |
| 99 |  | IL5 | 4.0 | 95.0 | Samples with only PSD results |
| 100 |  | IL5 | 5.0 | 94.0 | Samples with only PSD results |
| 101 |  | IL6 | 1.0 | 98.0 | Samples with only PSD results |
| 102 |  | IL6 | 2.0 | 97.0 | Samples with only PSD results |
| 103 |  | IL6 | 3.0 | 96.0 | Samples with only PSD results which had to be diluted prior to DLS use |
| 104 |  | IL6 | 4.0 | 95.0 | Samples with only PSD results |
| 105 |  | IL6 | 5.0 | 94.0 | Samples with only PSD results which had to be diluted prior to DLS use |
| 106 | 60 | None | — | 99.0 | Samples with only PSD results which had to be diluted prior to DLS use |
| 107 |  | IL2 | 1.0 | 98.0 | Samples with only PSD results |
| 108 |  | IL2 | 2.0 | 97.0 | Samples with only PSD results |
| 109 |  | IL2 | 3.0 | 96.0 | Samples with only PSD results which had to be diluted prior to DLS use |
| 110 |  | IL2 | 4.0 | 95.0 | Samples with only PSD results which had to be diluted prior to DLS use |
| 111 |  | IL2 | 5.0 | 94.0 | Samples with only PSD results which had to be diluted prior to DLS use |
| 112 |  | IL5 | 1.0 | 98.0 | Samples with only PSD results which had to be diluted prior to DLS use |
| 113 |  | IL5 | 2.0 | 97.0 | Samples with only PSD results which had to be diluted prior to DLS use |
| 114 |  | IL5 | 3.0 | 96.0 | Samples with only PSD results |
| 115 |  | IL5 | 4.0 | 95.0 | Samples with only PSD results |
| 116 |  | IL5 | 5.0 | 94.0 | Samples with only PSD results |
| 117 |  | IL6 | 1.0 | 98.0 | Samples with only PSD results which had to be diluted prior to DLS use |
| 118 |  | IL6 | 2.0 | 97.0 | Samples with only PSD results |
| 119 |  | IL6 | 3.0 | 96.0 | Samples with only PSD results which had to be diluted prior to DLS use |
| 120 |  | IL6 | 4.0 | 95.0 | Samples with only PSD results which had to be diluted prior to DLS use |
| 121 |  | IL6 | 5.0 | 94.0 | Samples with only PSD results which had to be diluted prior to DLS use |

Sonication Time 10 Minutes

Firstly, a set of samples were prepared with a fixed concentration of ss-Fe$_3$O$_4$ and variable concentration of different ILs. It is worth mentioning that ss-Fe$_3$O$_4$ is poorly synthesized nanoparticles and it is difficult to disperse it even in water. All the samples prepared displayed a precipitate and a stable supernatant. The supernatants showed good stability with all polydispersity indices being close to 0.2 and most cumulative diameter's being close to 60 nm. Sample 78 had a small PDI but the diameter was much larger than the other samples with the same IL which may be a results of the lower energy input during sonication. However, the other samples with energy inputs close to 14000 did not experience a change in diameter or PDI from other samples. So far, there is no strong discernable trend that indicates higher IL concentration leads to smaller PSD.

TABLE 16

Sonication and PSD parameters for samples 74-86. PSD results obtained from supernatants collected after 24 hours.

| Sample | IL | IL wt % | Sonication Time (min.) | Energy Input (J) | Sample Dilution Concentration (vol %) | Cumulative Diameter (nm) | PDI |
|---|---|---|---|---|---|---|---|
| 74 | None | 0 | 10 | 25664 | — | — | — |
| 75 | IL2 | 1 |  | 14313 | — | 54.1 | 0.197 |
| 76 | IL2 | 2 |  | 25292 | — | 59.5 | 0.209 |
| 77 | IL2 | 3 |  | 14622 | — | 63.1 | 0.224 |
| 78 | IL2 | 4 |  | 28386 | — | 60.8 | 0.187 |
| 79 | IL2 | 5 |  | 25606 | — | 69.4 | 0.221 |
| 80 | IL5 | 1 |  | 26213 | — | 63.6 | 0.203 |
| 81 | IL5 | 2 |  | 25276 | — | 65.2 | 0.197 |
| 82 | IL5 | 3 |  | 25225 | — | 68.6 | 0.223 |
| 83 | IL5 | 4 |  | 24789 | — | 67.4 | 0.227 |
| 84 | IL5 | 5 |  | 24242 | — | 81 | 0.185 |
| 85 | IL6 | 1 |  | 25614 | — | 64.1 | 0.154 |
| 86 | IL6 | 2 |  | 25665 | — | 64 | 0.156 |
| 87 | IL6 | 3 |  | 26343 | — | 64.9 | 0.188 |
| 88 | IL6 | 4 |  | 27360 | — | 66.4 | 0.197 |
| 89 | IL6 | 5 |  | 27293 | — | 67.2 | 0.21 |

Sonication Time 30 Minutes

In order to increase the dispersibility of Fe$_3$O$_4$ the sonication time was increased to 30-minute. Several samples were prepared and tested suing PSD. After decanting, the supernatants of the samples sonicated for 30 minutes displayed a much darker color than those sonicated for 10 minutes. They also took on a red hue when held up to light, whereas the samples sonicated for 10 minutes appeared to be light amber colored.

Table 17 is a summary of the sonication and PSD conditions of the samples prepared. Some of the samples, particularly the ones that were sonicated for 30 minutes, had supernatants which were too concentrated to give an accurate measurement on the DLS. These samples were diluted based on vol % and their PSD measurements aligned with those taken previously (~60 nm diameter and ~0.2 PDI).

TABLE 17

Sonication and PSD parameters for 30 minute sonication samples 90-105 (with IL2, IL5, or IL6).

| Sample | IL | IL wt % | Sonication Time (min.) | Energy Input (J) | Sample Dilution Concentration (vol %) | Cumulative Diameter (nm) | PDI |
|---|---|---|---|---|---|---|---|
| 90 | None | 0 | 30 | 79319 | — | N/A | N/A |
| 91 | IL2 | 1 | | 79492 | — | 57.8 | 0.173 |
| 92 | IL2 | 2 | | 81761 | — | 59 | 0.176 |
| 93 | IL2 | 3 | | 79452 | — | 57.8 | 0.211 |
| 94 | IL2 | 4 | | 60000* | — | 55.4 | 0.176 |
| 95 | IL2 | 5 | | 99603 | — | 59.9 | 0.176 |
| 96 | IL5 | 1 | | 48532 | — | 61.8 | 0.193 |
| 97 | IL5 | 2 | | 76675 | 33 | 63.2 | 0.182 |
| 98 | IL5 | 3 | | 79478 | 33 | 60.5 | 0.161 |
| 99 | IL5 | 4 | | 75907 | 33 | 66.2 | 0.22 |
| 100 | IL5 | 5 | | 76934 | 50 | 59.8 | 0.201 |
| 101 | IL6 | 1 | | 78609 | 50 | 60.5 | 0.178 |
| 102 | IL6 | 2 | | 78535 | 50 | 61.7 | 0.169 |
| 103 | IL6 | 3 | | 78732 | — | 63.7 | 0.185 |
| 104 | IL6 | 4 | | 78693 | 50 | 66.6 | 0.226 |
| 105 | IL6 | 5 | | 77496 | — | 63.1 | 0.174 |

Sonication Time 60 Minutes

Another set of samples were prepared but the sonication time was increased to 60 minutes. The control sample (DB106) was heavily precipitated after sonication and very similar to the control samples for the other sonication times (DB74 and DB90). All samples took on a dark black color after sonication. After decanting, the supernatants for all samples were a dark amber color.

The energy inputs for all samples sonication for 60 minutes was around 155000 J, and all samples had similar PSD results that align with previous trials as well (Table 18). Similar to the samples with 30 minutes sonication, some samples had to be diluted with dodecane before the DLS could accurately measure the PSD. The concentration of sample DB106 was too low to obtain a reliable PSD measurement.

TABLE 18

Sonication and PSD parameters for 60 minute sonication samples (IL2, IL5, or IL6).

| Sample | IL | IL wt % | Sonication Time (min.) | Energy Input (J) | Sample Dilution Concentration (vol %) | Cumulative Diameter (nm) | PDI |
|---|---|---|---|---|---|---|---|
| 106 | None | 0 | 60 | 154838 | N/A | N/A | N/A |
| 107 | IL2 | 1 | | 151225 | 50 | 57.2 | 0.172 |
| 108 | IL2 | 2 | | 152958 | 50 | 55.5 | 0.172 |
| 109 | IL2 | 3 | | 154193 | — | 58.6 | 0.175 |
| 110 | IL2 | 4 | | 155993 | — | 57.1 | 0.158 |
| 111 | IL2 | 5 | | 152862 | — | 60.9 | 0.205 |
| 112 | IL5 | 1 | | 153079 | — | 58.3 | 0.173 |
| 113 | IL5 | 2 | | 153699 | — | 59.5 | 0.172 |
| 114 | IL5 | 3 | | 156552 | 50 | 58.4 | 0.185 |
| 115 | IL5 | 4 | | 155271 | 50 | 58.6 | 0.186 |
| 116 | IL5 | 5 | | 155859 | 50 | 59.9 | 0.176 |
| 117 | IL6 | 1 | | 155238 | — | 58 | 0.158 |
| 118 | IL6 | 2 | | 156410 | 50 | 59.1 | 0.163 |
| 119 | IL6 | 3 | | 157297 | — | 61.9 | 0.173 |
| 120 | IL6 | 4 | | 155868 | — | 60.5 | 0.187 |
| 121 | IL6 | 5 | | 156943 | 50 | 62.3 | 0.215 |

Summary of ICP-MS Data for Different Sonication Time

The following table and figures summarize previous and recent the ICP-MS results obtained for all SkySpring Iron Oxide samples (74-121) prepared using the procedure explained earlier.

Figure 9:
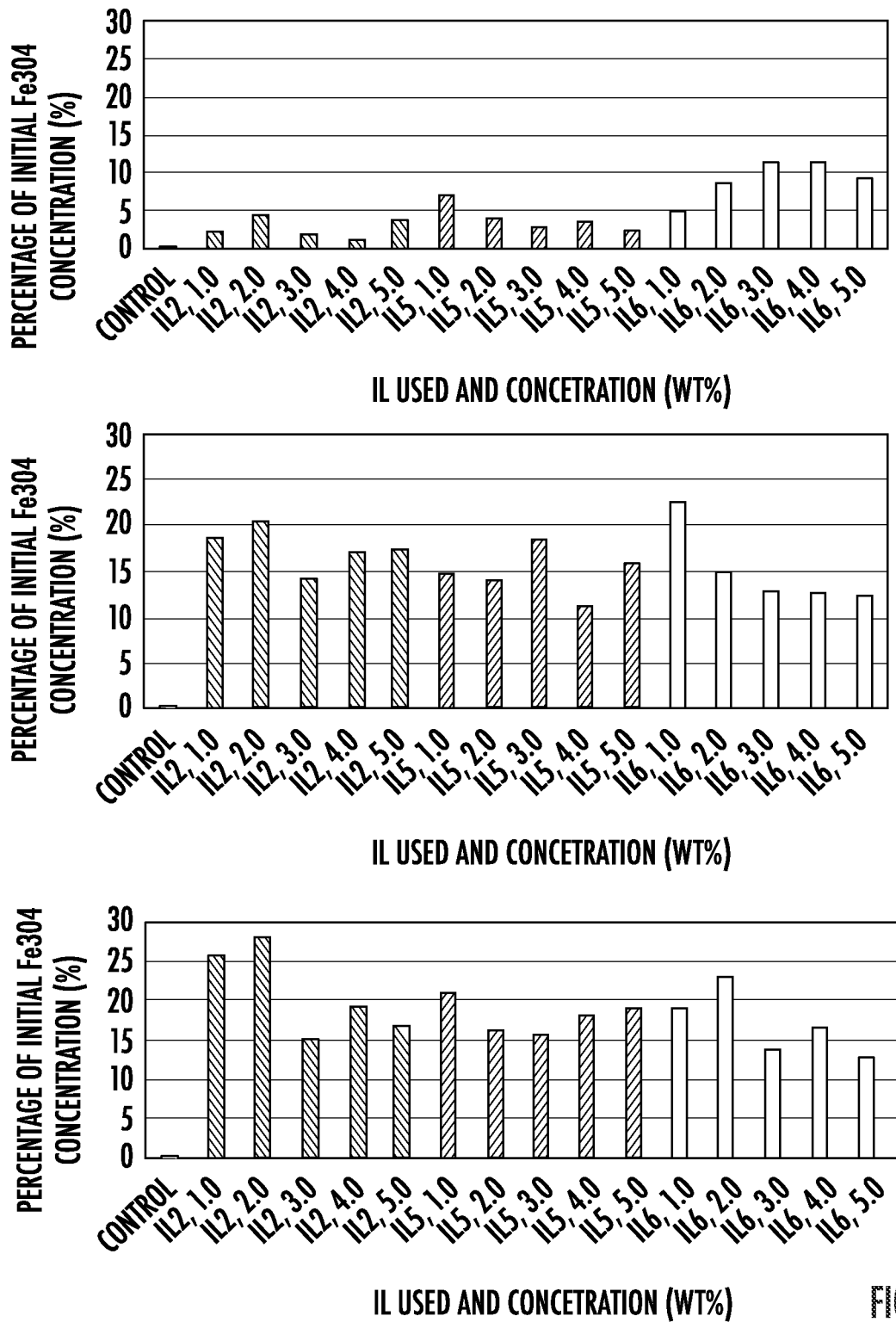
FIG. 9 includes three bar graphs, illustrating the percentage $Fe_3O_4$ remaining in (a) samples 74-89 containing IL2, IL5, and IL6 at 1.0-5.0 wt % sonicated for 10 minutes, (b) samples 90-105 containing IL2, IL5, and IL6 at 1.0-5.0 wt % sonicated for 30 minutes, and (c) samples 106-121 containing IL2, IL5, and IL6 at 1.0-5.0 wt % sonicated for 60 minutes.

In order to determine the concentrations of $Fe_3O_4$ acid digestion was done on the supernatants, following by analysis of iron concentration using both hydrogen and helium gases through the ICP-MS. As shown in the table, the use of ILs significantly enhance the dispersibility of ss-$Fe_3O_4$. Compared to the control that does not have any stabilizer, nearly all the nanoparticles precipitated immediately after sonication. It is worth mentioning that ss-$Fe_3O_4$ purchased from SkySpring company is a poorly synthesized nanoparticles and this leads to very poor dispersibility even with the addition of ILs. However, comparing the samples with and without ILs, it is evident that the ILs addition significantly enhance the dispersibility of ss-$Fe_3O_4$. See Table 19 for 10 minutes sonication, Table 20 for 30 minutes sonication, and Table 21 for 60 minutes sonication, for a summary of the results. FIG. 9 shows the percentage $Fe_3O_4$ remaining in (a) samples 74-89 containing IL2, IL5, and IL6 at 1.0-5.0 wt % sonicated for 10 minutes, (b) samples 90-105 containing IL2, IL5, and IL6 at 1.0-5.0 wt % sonicated for 30 minutes, and (c) samples 106-121 containing IL2, IL5, and IL6 at 1.0-5.0 wt % sonicated for 60 minutes.

The following sample calculation using data from sample 75 (1.0 wt % IL2, sonicated for 10 minutes):

$$\text{Fe mass fraction} = \frac{M_{Fe_3O_4}}{3 \times M_{Fe}}$$

$$\text{Fe mass fraction} = \frac{231.5476 \text{ g/mol}}{167.55 \text{ g/mol}}$$

Fe mass fraction = 0.7236

$$[Fe_3O_4] = \frac{[Fe]}{\text{Fe mass fraction}}$$

$$[Fe_3O_4] = \frac{117.246 \text{ ppm}}{0.7236}$$

$$[Fe_3O_4] = 162.0 \text{ ppm}$$

TABLE 19

ICP-MS data for concentration of Fe remaining in samples 74-121 with different concentrations of IL2, IL5, and IL6 at 1.0-5.0 wt %, sonicated for 10 minutes.

| Sample | Sonication Time (min.) | IL | IL wt % | Initial Concentration of $Fe_3O_4$ (ppm) | Supernatant Concentration of $Fe_3O_4$ (ppm) | Percentage Concentration Remaining (%) |
|---|---|---|---|---|---|---|
| 74 | 10 | None | 0 | 7575.78 | 0.49 | 0.006 |
| 75 | | IL2 | 1 | 7585.87 | 162.03 | 2.14 |
| 76 | | IL2 | 2 | 7596.00 | 339.32 | 4.47 |
| 77 | | IL2 | 3 | 7606.17 | 126.82 | 1.67 |
| 78 | | IL2 | 4 | 7616.36 | 86.82 | 1.14 |
| 79 | | IL2 | 5 | 7626.58 | 280.12 | 3.67 |
| 80 | | IL5 | 1 | 7585.80 | 519.99 | 6.84 |
| 81 | | IL5 | 2 | 7595.87 | 297.59 | 3.92 |
| 82 | | IL5 | 3 | 7605.96 | 215.09 | 2.83 |
| 83 | | IL5 | 4 | 7616.08 | 275.19 | 3.61 |
| 84 | | IL5 | 5 | 7626.23 | 169.70 | 2.22 |
| 85 | | IL6 | 1 | 7585.37 | 391.12 | 5.16 |
| 86 | | IL6 | 2 | 7595.01 | 654.47 | 8.62 |
| 87 | | IL6 | 3 | 7604.67 | 873.27 | 11.48 |
| 88 | | IL6 | 4 | 7614.36 | 869.01 | 11.41 |
| 89 | | IL6 | 5 | 7624.07 | 715.24 | 9.38 |

TABLE 20

ICP-MS data for concentration of Fe remaining in samples 74-121 with different concentrations of IL2, IL5, and IL6 at 1.0-5.0 wt %, sonicated for 30 minutes.

| Sample | Sonication Time (min.) | IL | IL wt % | Initial Concentration of $Fe_3O_4$ (ppm) | Supernatant Concentration of $Fe_3O_4$ (ppm) | Percentage Concentration Remaining (%) |
|---|---|---|---|---|---|---|
| 90 | 30 | None | 0 | 7575.78 | 0.69 | 0.009 |
| 91 | | IL2 | 1 | 7585.87 | 1432.52 | 18.88 |
| 92 | | IL2 | 2 | 7596.00 | 1558.74 | 20.52 |
| 93 | | IL2 | 3 | 7606.17 | 1075.77 | 14.14 |
| 94 | | IL2 | 4 | 7616.36 | 1302.99 | 17.11 |
| 95 | | IL2 | 5 | 7626.58 | 1331.61 | 17.46 |
| 96 | | IL5 | 1 | 7585.80 | 1117.09 | 14.73 |
| 97 | | IL5 | 2 | 7595.87 | 1072.89 | 14.12 |
| 98 | | IL5 | 3 | 7605.96 | 1401.52 | 18.43 |
| 99 | | IL5 | 4 | 7616.08 | 867.86 | 11.39 |
| 100 | | IL5 | 5 | 7626.23 | 1217.35 | 15.96 |
| 101 | | IL6 | 1 | 7585.37 | 1721.23 | 22.69 |
| 102 | | IL6 | 2 | 7595.01 | 1147.10 | 15.10 |
| 103 | | IL6 | 3 | 7604.67 | 983.22 | 12.93 |
| 104 | | IL6 | 4 | 7614.36 | 960.51 | 12.59 |
| 105 | | IL6 | 5 | 7624.07 | 958.05 | 12.57 |

TABLE 21

ICP-MS data for concentration of Fe remaining in samples 74-121 with different concentrations of IL2, IL5, and IL6 at 1.0-5.0 wt %, sonicated for 60 minutes.

| Sample | Sonication Time (min.) | IL | IL wt % | Initial Concentration of $Fe_3O_4$ (ppm) | Supernatant Concentration of $Fe_3O_4$ (ppm) | Percentage Concentration Remaining (%) |
|---|---|---|---|---|---|---|
| 106 | 60 | None | 0 | 7575.78 | 1.88 | 0.02 |
| 107 | | IL2 | 1 | 7585.87 | 1942.54 | 25.61 |
| 108 | | IL2 | 2 | 7596.00 | 2115.05 | 27.84 |
| 109 | | IL2 | 3 | 7606.17 | 1149.07 | 15.11 |
| 110 | | IL2 | 4 | 7616.36 | 1473.28 | 19.34 |
| 111 | | IL2 | 5 | 7626.58 | 1276.02 | 16.73 |
| 112 | | IL5 | 1 | 7585.80 | 1587.61 | 20.93 |
| 113 | | IL5 | 2 | 7595.87 | 1228.65 | 16.17 |
| 114 | | IL5 | 3 | 7605.96 | 1197.89 | 15.75 |
| 115 | | IL5 | 4 | 7616.08 | 1391.82 | 18.27 |
| 116 | | IL5 | 5 | 7626.23 | 1460.13 | 19.15 |
| 117 | | IL6 | 1 | 7585.37 | 1451.92 | 19.14 |
| 118 | | IL6 | 2 | 7595.01 | 1748.22 | 23.02 |
| 119 | | IL6 | 3 | 7604.67 | 1044.164 | 13.73 |
| 120 | | IL6 | 4 | 7614.36 | 1269.35 | 16.67 |
| 121 | | IL6 | 5 | 7624.07 | 968.44 | 12.70 |

Dispersion of Aeroxide Alu C in Dodecane

The state of the dispersions of AluC in dodecane, from stable dispersion to agglomeration, with two different reagents (IL2, IL6) is needed to be studied in order to determine the mobility and the minimum dispersion ILs wt %. The difference between the two nanoparticles' behavior was also being investigated since they have different polarity and physical characteristics. The following revised procedure from last week was used:

1. Prepare a mixture of dodecane with IL2 and IL6 held at 1.0 wt % and stir for 5 minutes (anywhere from 500-700 rpm) with a magnetic stirrer
2. Add a fixed concentration of AluC (1 wt %) to the solution using a funnel and occasionally shaking
3. Sonicate for 5 minutes (30 sec. on, 30 sec off) with a 420-B tip at 50% amplitude in an ice-water bath
4. Take pictures, measure PSD (quartz cuvette), and measure average mobility of the particles (low conductivity cell in 2 ml)
5. Observe visually for a few days All the samples were prepared of 15 grams (around 20 mL) in 30 mL beaker and sonicated with a solid tip probe (420B). It is worth mention that since the compositions of the samples are the same compared to Aerosil-200 samples, the same weight ratio was used for preparation. In addition, the sonication time was extended to 5 minutes in order to completely disperse the samples.

Table 22 shows the composition of the samples prepared with IL2 and Alu C in Dodecane along with the sonication energy. While Table 23 shows the composition of the samples prepared with IL6.

TABLE 22

Sample Composition with IL1, Alu C, and Dodecane

| Sample Name | IL2, wt % | Calculated IL2 (g) | Weighted IL2 (g) | Alu C, wt % | Alu C (g) | Weighted Alu C (g) | Dodecane (g) | Weighted Dodecane | Sonication Energy (J) |
|---|---|---|---|---|---|---|---|---|---|
| AS34 | 5 | 0.8096 | 0.8094 | 1 | 0.15 | 0.1504 | 14.0404 | 14.0401 | 14059 |
| AS35 | 1 | 0.1619 | 0.1622 | 1 | 0.15 | 0.1499 | 14.6881 | 14.6881 | 13855 |
| A536 | 0.5 | 0.081 | 0.0814 | 1 | 0.15 | 0.1502 | 14.769 | 14.7693 | 13310 |
| AS37 | 0.1 | 0.0162 | 0.016 | 1 | 0.15 | 0.1505 | 14.8338 | 14.8338 | 13298 |
| AS38 | 0.05 | 0.0081 | 0.0081 | 1 | 0.15 | 0.1498 | 14.8419 | 14.8418 | 14275 |
| A539 | 0.01 | 0.0016 | 0.0017 | 1 | 0.15 | 0.1502 | 14.8484 | 14.8487 | 13215 |

TABLE 23

Sample Composition with IL6, AluC, and Dodecane

| Sample Name | IL6, wt % | Calculated IL6 (g) | Weighted IL6 (g) | AluC, wt % | AluC (g) | Weighted AluC (g) | Dodecane (g) | Weighted Dodecane | Sonication Energy (J) |
|---|---|---|---|---|---|---|---|---|---|
| AS40 | 5 | 0.7999 | 0.8001 | 1 | 0.15 | 0.1500 | 14.0501 | 14.0504 | 14162 |
| AS41 | 1 | 0.1600 | 0.1598 | 1 | 0.15 | 0.1497 | 14.6900 | 16.6904 | 14231 |
| AS42 | 0.5 | 0.0800 | 0.0799 | 1 | 0.15 | 0.1503 | 14.7700 | 14.7700 | 14350 |
| AS43 | 0.1 | 0.0160 | 0.0165 | 1 | 0.15 | 0.1496 | 14.8340 | 14.8340 | 15999 |
| AS44 | 0.05 | 0.0080 | 0.0081 | 1 | 0.15 | 0.1496 | 14.8420 | 14.8422 | 17206 |
| AS45 | 0.01 | 0.0016 | 0.0015 | 1 | 0.15 | 0.1502 | 14.8484 | 148482 | 16093 |

In general, a longer sonication time means more sonication energy was input into the solution. The DLS measurement and visual observations were expected to be different from the Aerosil-200.

Visual Observations

Firstly, the samples were inspected visually after sonication and photographs were taken. For dispersions prepared with IL2, based on the visual observation, for sample AS38, AS39 there are white precipitations at the bottom of the vial (precipitated 10 minutes after sonication), there are also transparent solid that sticks on the wall of the vials in these samples. Samples are cloudier compared to the solution that was made from Aerosil-200, and they are considered as translucent solutions instead of transparent solutions (Aerosil-200). Table 24 provides a detailed discussion of the visual observations of the sample from AS34 to AS39.

TABLE 24

Visual observations of the sample from AS22 to AS27

| Sample Name | Visual Observations |
|---|---|
| AS34 | Low viscosity, could flow like dodecane solvent<br>A yellowish color, translucent solution, the solution shows orange color under the light<br>No precipitation after a few days of preparation |
| AS35 | Low viscosity, could flow like dodecane solvent<br>A lighter yellowish color, translucent solution, the solution shows orange color under the light<br>No precipitation after a few days of preparation |
| AS36 | Low viscosity, could flow like dodecane solvent<br>Almost white color, translucent<br>No precipitation after a few days of preparation |
| AS37 | Low viscosity, could flow like dodecane solvent<br>A white color solution, translucent<br>No precipitation after a few days of preparation |
| AS38 AS39 | More viscous than the dispersed samples more cloudy, the precipitations could be seen in the vail<br>Clear separations of precipitates and solvents after 10 minutes of sonication. |

For dispersions prepared with IL5, for sample AS43, AS44 and AS45 there are white precipitations at the bottom of the vial (precipitated 10 minutes after sonication), there are also transparent solid that sticks on the wall of the vials in these samples. Table 25 provides a detailed discussion of the visual observations of the sample from AS40 to AS45.

TABLE 25

Visual observations of the sample from AS28 to AS30.

| Sample Name | Visual Observations |
|---|---|
| AS40 | Low viscosity, could flow like dodecane solvent<br>A light yellowish color, translucent solution, the solution shows a light orange color under the light. Similar to AS35.<br>No precipitation after a few days of preparation |
| AS41 | Low viscosity, could flow like dodecane solvent<br>A white color solution, translucent<br>No precipitation after a few days of preparation |
| AS42 | Low viscosity, could flow like dodecane solvent<br>White color, translucent<br>No precipitation after a few days of preparation |
| AS43 AS44 AS45 | More viscous than the dispersed samples<br>more cloudy, the precipitations could be seen in the vail after the sonication<br>Clear separations of precipitates and solvents after 10 minutes of sonication. |

Sample AS40, AS41, and AS42 were expecting to be the dispersed sample, as there was no precipitations and solid-solvent separations among these samples. DLS measurement was used for these samples to prove the state of dispersion.

DLS Measurements

Based on the visual observation, DLS measurements were conducted for all the non-precipitated samples prepared with IL2. These samples were expected to be dispersed (Table 26). For the samples prepared with IL6 (A540-A545), the sample AS40-AS42 were not having observable precipitations or agglomeration after the sonication, whereas the other three samples were agglomerated after the sample sonication. (Table 27).

TABLE 26

DLS measurements for AluC dispersions in Dodecane using IL1 (AS34 to AS37)

| Sample Name | IL2 (wt %) | Cumulant Diameter (nm) | Polydispersity index | Mobility(cm$^2$/Vs) |
|---|---|---|---|---|
| AS34 | 5 | 183.300 | 0.192 | −4.053E−06 |
| AS35 | 1 | 159.400 | 0.160 | 4.246E−07 |
| AS36 | 0.5 | 158.100 | 0.159 | −3.082E−06 |
| AS37 | 0.1 | 153.300 | 0.133 | −6.647E−08 |

As expected, the samples AS33 to AS37 are dispersed. The samples have similar particle sizes, the average particle sizes are ranging from 150 to 183, with around 0.15 PDI. The cumulant diameter has a decreasing trend, this trend may result from IL2 concentration difference in samples; the samples that have higher ILs wt % require more energy to disperse the samples completely. Since the sonication times were the same, more concentrated samples would have a higher cumulant diameter.

Table 27 also shows a similar PSD decreasing trend as IL6 was used instead.

TABLE 27

DLS measurements for AluC dispersions in Dodecane using IL6 (AS40 to AS42)

| Sample Name | IL6 (wt %) | Cumulated Diameter (nm) | Polydispersity Index | Mobility(cm$^2$/Vs) |
|---|---|---|---|---|
| AS40 | 5 | 267.000 | 0.123 | −1.330E−07 |
| AS41 | 1 | 152.200 | 0.146 | −8.657E−07 |
| AS42 | 0.5 | 153.300 | 0.146 | −7.480E−07 |

The PSD measurements were conducted for dispersed samples using IL1 (5 wt % to 0.1 wt %) & IL5 (5 wt % to 0.5 wt %), Alu C in dodecane.

Most strikingly, the minimum dispersion IL2 concentration for Alu C nanoparticles is lower than Aerosil-200 (between 0.1-0.05 wt % for Alu C), similar behavior was also being found from the samples that were prepared by IL6 (between 0.5-0.1 wt % for Alu C). Since a similar change was observed for both ILs samples, it is possible that the particle charge characteristic of the ILs and nanoparticles are the major factor for the dispersion of these samples. As for the differences between IL2 and IL6, there are more samples that are dispersed for IL2, this may result from the steric interactions of IL6. However, this might be the minor factor, since there is no huge difference for the minimum dispersion concertation for IL2 and IL6.

The sample with 5 wt % IL6 has a wider range of particle sizes, this may due to the high concentration of the IL6 used (5 wt %) in this sample, the sample may not be fully sonicated to form an identical particle size.

The mobility tests were focused on the dispersed samples, as the ILs differences, two separated graphs are used to investigate the mechanism of the solution. All experiments were conducted under source voltage of 45 mV.

Figure 10:
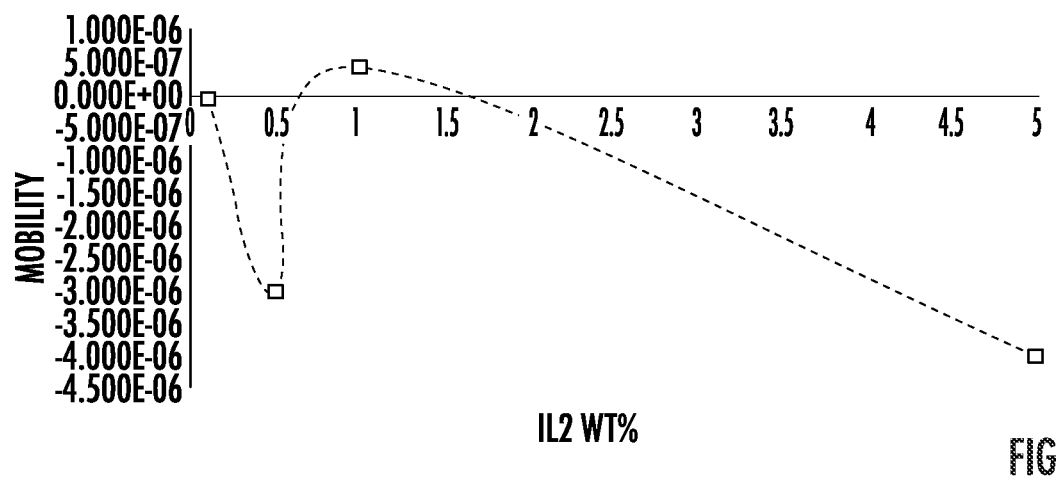
FIG. 10 is a line graph illustrating the mobility of AluC Coated with IL2 in dodecane (1 wt % AluC).

The mobility graph (FIG. 10) has a general trend similar to the A-200, IL2 samples, as the 1 wt % sample has a different polarity compared to the other samples. The 1:1 wt % ratio of nanoparticle and IL2 has a polarity difference, more literature review is needed to prove this observation. It is also possible that the data collected is not accurate enough as the mobility test for the low conductivity solutions is not fully developed. In addition, the characteristic change regarding the sonicated samples may also affect the experiment result (viscosity, dielectric constant).

Figure 11:
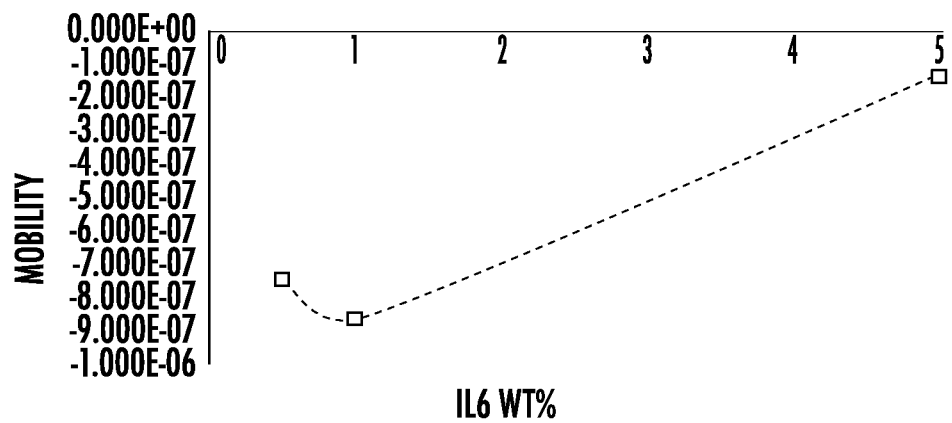
FIG. 11 is a line graph illustrating the mobility of AluC Coated with IL6 in dodecane (1 wt % AluC).

As for the samples that used IL6 as the coating chemicals (FIG. 11), the polarity remains the same. The mobility is expected to be closer to 0 when more IL6 is used; 1 wt % IL6 sample has the highest mobility.

It is worth mentioning that the sample that was put into the cell tends to change the polarity when the second trial is being conducted for the same exact sample. As a result, the same sample cannot be run twice continuously in the low conductivity cell for any other future experiments.

Dispersion of Carbon Black in Dodecane

Carbon black (Vulcan XC 72R from Cabot with 50 nm size) was tested in order to get some insight on whether the stabilizing theory with ILs is working non-oxide nanoparticles. The preparation of the samples AS 58 (1 wt % IL2), 59 (0 wt % IL2), 60 (0.5 wt % IL2), 61 (0.1 wt % IL2), and 62 (0.05 wt % IL2) have followed the same method that was used for Aerosil-200 and AluC; all these samples were sonicated in 2 minutes. The first two samples with 1 wt % (AS58) and 0 wt % (AS59) of IL2 were prepared respectively to investigate the behavior of carbon black, which determines whether the follow-up tests should be prepared within the range between 1 wt % and 0 wt % (IL2 concentration) or not. For this week, all the samples were prepared using the vials instead of the beakers. Following detailed procedure was followed for the preparation of these samples.

1. Prepare a mixture of dodecane with IL2 with different wt % and stir for 5 minutes (anywhere from 500-700 rpm) with a magnetic stirrer
2. Add a fixed concentration of carbon black (0.1 wt %) to the solution using a funnel and occasionally shaking (wear face masks during the weighting and adding process)
3. Sonicate for 2 minutes (30 sec. on, 30 sec off) with a 420-A microprobe at 50% amplitude in an ice-water bath
4. Take pictures, measure PSD (quartz cuvette), and measure average mobility of the particles (low conductivity cell in 2 ml)
5. Observe visually for a few days Table 28 shows the composition of the samples prepared with IL2 and carbon black in Dodecane along with the sonication energy.

TABLE 28

| Sample Name | IL2, wt % | Calculated IL2 (g) | Weighted IL2 (g) | Carbon Black, wt % | Carbon Black (g) | Weighted Carbon Black (g) | Dodecane (g) | Weighted Dodecane | Sonication Energy (J) |
|---|---|---|---|---|---|---|---|---|---|
| AS58 | 1 | 0.1619 | 0.1615 | 0.1 | 0.015 | 0.0152 | 14.8231 | 14.8234 | 4020 |
| AS60 | 0.5 | 0.0810 | 0.0807 | 0.1 | 0.015 | 0.0152 | 14.9040 | 14.9042 | 3753 |

TABLE 28-continued

| Sample Name | IL2, wt % | Calculated IL2 (g) | Weighted IL2 (g) | Carbon Black, wt % | Carbon Black (g) | Weighted Carbon Black (g) | Dodecane (g) | Weighted Dodecane | Sonication Energy (J) |
|---|---|---|---|---|---|---|---|---|---|
| AS61 | 0.1 | 0.0162 | 0.0162 | 0.1 | 0.015 | 0.0154 | 14.9688 | 14.9694 | 3728 |
| AS62 | 0.05 | 0.0081 | 0.0081 | 0.1 | 0.015 | 0.0146 | 14.9769 | 14.9769 | 3740 |
| AS59 | 0 | 0.0000 | 0.0000 | 0.1 | 0.015 | 0.0153 | 14.9850 | 14.9850 | 3741 |

Visual Observations

Figure 12:
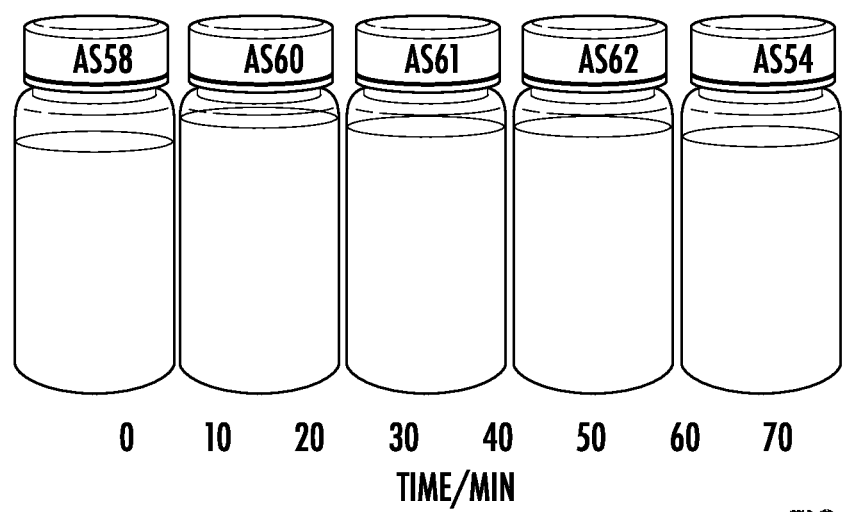
FIG. 12 is a photograph of samples with different concentrations of IL2 with carbon black in dodecane after 1 week, AS58 (1 wt %), AS60 (0.5 wt %), AS61 (0.1 wt %), AS62 (0.05 wt %) and AS59 (0 wt %) (Photo took after two days of sonication).

FIG. 12 shows the photographs of samples with different concentrations of IL2 with carbon black in dodecane after 1 week, AS58 (1 wt %), AS60 (0.5 wt %), AS61 (0.1 wt %), AS62 (0.05 wt %) and AS59 (0 wt %) (Photo took after two days of sonication). The dispersion prepared with no IL2 added (AS59) was seen to separate and precipitate with 2 h after sonication. meanwhile, the samples prepared with different concentrations of IL2 did not show any separation for at least few days. Since it was hard to observe the precipitation and dispersion behaviors for these samples, the DLS tests were conducted for all the samples. Table 29 provides a detailed discussion of the visual observations of the sample from AS58 to AS62.

TABLE 29

Visual observations of the sample from AS58 to AS62

| Sample Name | Visual Observations |
|---|---|
| AS58 | Low viscosity, could flow like dodecane solvent<br>A deep black color, opaque solution, the solution shows no transparency under light<br>No precipitation after a few days of preparation |
| AS60<br>AS61<br>AS62 | Low viscosity, could flow like dodecane solvent<br>Bigger deep black particles floating in the lighter black solution<br>No precipitation after a few days of preparation<br>Low viscosity, could flow like dodecane solvent<br>No precipitation after a few days of preparation |
| AS59 | Different level of black color in different heights of the vail after sonication<br>Clear separations of precipitates and solvents after 3 hours of sonication. |

DLS Measurements

Based on the visual observation, DLS measurements were conducted for all the non-precipitated samples prepared with IL2, since the carbon black samples precipitations were hard to observe shortly after the sonication; all the samples were tested in order to prove whether the samples were dispersed or not (Table 30), however, sample AS59 was precipitated after the PSD test. It is worth mention that due to the opaque characteristic of the carbon black samples, the mobility test samples were diluted in 1 (original solution): 9 (dodecane) volume ratio.

TABLE 30

DLS measurements for Carbon Black dispersions in Dodecane using IL2 (AS58 to AS62)

| Sample Name | IL2 (wt %) | Cumulant Diameter (nm) | Polydispersity index | Mobility($cm^2$/Vs) | standard deviation |
|---|---|---|---|---|---|
| AS58 | 1 | 1723.9 | 0.382 | 2.034E−06 | 1.491E−05 |
| AS60 | 0.5 | 1420.1 | 0.466 | −2.115E−06 | 1.178E−05 |
| AS61 | 0.1 | 1285.1 | 0.229 | −7.257E−07 | 4.757E−06 |

TABLE 30-continued

DLS measurements for Carbon Black dispersions in Dodecane using IL2 (AS58 to AS62)

| Sample Name | IL2 (wt %) | Cumulant Diameter (nm) | Polydispersity index | Mobility($cm^2$/Vs) | standard deviation |
|---|---|---|---|---|---|
| AS62 | 0.05 | 1233.8 | 0.018 | −2.078E−05 | 1.194E−04 |
| AS59 | 0 | 4856 | 0.217 | 8.761E−07 | 1.435E−05 |

For the samples that have IL2, the cumulant diameters are decreasing as the wt % of IL1 is decreasing. For mobility tests, except the sample AS58 and AS59, all other samples have negative average mobility. In addition, the standard deviation data are all different. In general, the higher the mobility the higher the STD, which means the difference between each trail is higher for the samples that have higher mobility.

REFERENCES

Comiskey, B., Albert, J. D., Yoshizawa, H., Jacobson, J. 1998. An electrophoretic ink for all-printed reflective electronic displays. *Nature* 394: 253. 10.1038/28349.

Hao, T. 2001. Electrorheological Fluids. *Advanced Materials* 13 (24): 1847-1857. doi:10.1002/1521-4095(200112)13:24<1847::AID-ADMA1847>3.0.CO;2-A.

Jones, S. A., Martin, G. P., Brown, M. B. 2006. Manipulation of Beclomethasone–Hydrofluoroalkane Interactions using Biocompatible Macromolecules. *Journal of Pharmaceutical Sciences* 95 (5): 1060-1074. 10.1002/jps.20608.

León, O., Rogel, E., Urbina, A., Andújar, A., Lucas, A. 1999. Study of the Adsorption of Alkyl Benzene-Derived Amphiphiles on Asphaltene Particles. *Langmuir* 15 (22): 7653-7657. 10.1021/Ia9812370.

Li, Z., Zhu, Y. 2003. Surface-modification of SiO2 nanoparticles with oleic acid. *Applied Surface Science* 211 (1): 315-320. http://doi.org/10.1016/50169-4332(03)00259-9.

McCrary, P. D., Beasley, P. A., Gurau, G., Narita, A., Barber, P. S., Cojocaru, O. A., Rogers, R. D. 2013. Drug specific, tuning of an ionic liquid's hydrophilic-lipophilic balance to improve water solubility of poorly soluble active pharmaceutical ingredients. *New Journal of Chemistry* 37 (7): 2196-2202. http://doi.org/10.1039/C3NJ00454F.

Morrison, I. D. 1993. Electrical charges in nonaqueous media. *Colloids and Surfaces A: Physicochemical and Engineering Aspects* 71 (1): 1-37. https://doi.org/10.1016/0927-7757(93)80026-B.

Poovarodom, S., Berg, J. C. 2010. Effect of particle and surfactant acid-base properties on charging of colloids in apolar media. *Journal of Colloid and Interface Science* 346 (2): 370-377. https://doi.org/10.1016/j.jcis.2010.03.012.

Ryoo, W., Webber, S. E., Bonnecaze, R. T., Johnston, K. P. 2006. Long-Ranged Electrostatic Repulsion and Crystallization of Emulsion Droplets in an Ultralow Dielectric Medium Supercritical Carbon Dioxide. *Langmuir* 22 (3): 1006-1015. 10.1021/la052298i.

Sainis, S. K., Germain, V., Mejean, C. O., Dufresne, E. R. 2008. Electrostatic Interactions of Colloidal Particles in Nonpolar Solvents: Role of Surface Chemistry and Charge Control Agents. *Langmuir* 24 (4): 1160-1164. 10.1021/la702432u.

The invention claimed is:

1. A method for stabilizing a dispersion of nanoparticles in a nonpolar solvent, comprising admixing with the nanoparticles in solvent stabilizing amounts of anionic species and cationic species, wherein the stabilizing amounts of the anionic species and the cationic species are such that the molar ratios of the anionic species and of the cationic species, respectively to the nanoparticles, are different, wherein the anionic species and the cationic species together form ionic or hydrogen bonds therebetween in the dispersion, wherein a first one of the anionic or the cationic species has a higher relative affinity for the nanoparticles in the solvent, and the other of the anionic or cationic species has a greater relative solubility in the nonpolar solvent than the first ionic species; and wherein the anionic and cationic species are together capable of forming an ionic compound that is soluble in the non-polar solvent to provide the anionic and cationic species in the stabilizing amounts;

wherein the dispersion is formed into a stable non-precipitating dispersion of the nanoparticles in the presence of the anionic and cationic species in the nonpolar solvent, under stabilized conditions for a stabilized period of time wherein, in the absence of the anionic and the cationic species, the nanoparticles would precipitate under the stabilized conditions within the stabilized period of time;

wherein the ionic compound is an ionic liquid at a temperature at which the dispersion is stabilized, or under the stabilized conditions; and, wherein the ionic liquid is N-butylammonium oleate ([C4NH3][oleate]), N-octylammonium oleate ([C8NH3][Oleate]) tri-ethylammonium oleate ([HN222][oleate]), tri-N-butylammonium oleate ([HN444][oleate]), tri-N-octylammonium oleate ([HN888][oleate]), N-octylammonium dodecylbenzenesulfonate ([C8NH3][DBS]), butylammonium dodecyl benzenesulfonate, tri-ethylammonium dodecyl benzenesulfonate, tri-N-butylammonium dodecyl benzenesulfonate, or tri-N-octylammonium dodecyl benzenesulfonate.

2. The method of claim 1, wherein the ionic liquid has a melting point below 200° C.

3. The method of claim 1, wherein the ionic liquid comprises a primary, secondary, or tertiary cyclic amine.

4. The method of claim 3, wherein the ionic liquid comprises a primary, secondary or tertiary alkyl amine.

5. The method of claim 1, wherein the ionic liquid comprises one or more primary carboxylic acid or sulfonic acid, saturated or unsaturated, alkyl sulfonic acid or primary, saturated or unsaturated alkyl benzene sulfonic acid.

6. The method of claim 1, wherein the nonpolar solvent has a dielectric constant of less than 15.

7. The method of claim 1, wherein the stabilized conditions comprise an average or maximum gravitational force during the stabilized period of 1 gravity and an ambient temperature or a temperature above a freezing point or below a boiling point of the dispersion.

8. The method of claim 1, wherein the nanoparticles comprise a nanoparticle that is comprised of a metal, a metalloid, a metal oxide, a metalloid oxide, carbon, cellulose or a mixture thereof.

9. The method of claim 8, wherein the metal or metalloid oxide comprises silicon oxide, iron oxide or aluminum oxide; the carbon comprises carbon black or carbon nanotubes; or, the cellulose comprises cellulose nanocrystals.

10. The method of claim 1, wherein the nanoparticles comprise a nanoparticle comprising an element selected from the group consisting of Fe, Al, Ag, Au, Co, Mo, N, Ni, Pd, Pt, S, Sn, Si, Ti, W, or Zn.

11. The method of claim 1, wherein the nanoparticles have an average dimension ranging from 1 nm to 100 nm.

12. The method of claim 1, wherein the nanoparticles comprise a nanoparticle that has a charged particle surface in the dispersion.

13. The method of claim 12, wherein the charged particle surface is positively charged.

14. The method of claim 12, wherein the charged particle surface is negatively charged.

15. The method of claim 1, wherein the nanoparticles comprise a nanoparticle that does not have a charged particle surface in the dispersion.

16. The method of claim 1, wherein the stabilization period is 1 day, 1 week, 1 month or 1 year.

17. The method of claim 1, wherein the nanoparticles are present in the dispersion in an amount ranging from 0.001 wt. % to 50 wt. % relative to the dispersion weight.

18. The method of claim 1, wherein a weight ratio of the combined anionic and cationic species to the nanoparticles in the dispersion ranges from 1:10 to 10:1 combined species to nanoparticles.

* * * * *